United States Patent
Rogers et al.

(10) Patent No.: US 12,419,570 B2
(45) Date of Patent: *Sep. 23, 2025

(54) THIN, SOFT, SKIN-MOUNTED MICROFLUIDIC NETWORKS FOR DETECTION AND ANALYSIS OF TARGETS OF INTEREST IN SWEAT

(71) Applicant: NORTHWESTERN UNIVERSITY, Evanston, IL (US)

(72) Inventors: John A. Rogers, Wilmette, IL (US); Tyler R. Ray, Evanston, IL (US); Jungil Choi, Chicago, IL (US); Yi Zhang, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 800 days.

This patent is subject to a terminal disclaimer.

(21) Appl. No.: 16/616,813

(22) PCT Filed: Jun. 1, 2018

(86) PCT No.: PCT/US2018/035674
§ 371 (c)(1),
(2) Date: Nov. 25, 2019

(87) PCT Pub. No.: WO2018/223044
PCT Pub. Date: Dec. 6, 2018

(65) Prior Publication Data
US 2020/0093416 A1    Mar. 26, 2020

Related U.S. Application Data
(60) Provisional application No. 62/514,515, filed on Jun. 2, 2017.

(51) Int. Cl.
*A61B 5/00* (2006.01)
*A61B 5/01* (2006.01)
(Continued)

(52) U.S. Cl.
CPC ............ *A61B 5/4266* (2013.01); *A61B 5/002* (2013.01); *A61B 5/01* (2013.01); *A61B 5/1032* (2013.01);
(Continued)

(58) Field of Classification Search
CPC ......... A61B 5/4266; A61B 5/002; A61B 5/01; A61B 5/1032; A61B 5/14532;
(Continued)

(56) References Cited

U.S. PATENT DOCUMENTS
4,960,467 A    10/1990 Peck
6,198,953 B1    3/2001 Webster et al.
(Continued)

FOREIGN PATENT DOCUMENTS
JP    H08313408 A    11/1996
JP    2002519641 A    7/2002
(Continued)

OTHER PUBLICATIONS
Koh et al., A soft, wearable microfluidic device for the capture, storage, and colorimetric sensing of sweat, Science Translational Medicine, 2016.
(Continued)

*Primary Examiner* — Elizabeth A Robinson
*Assistant Examiner* — Sophia Y Lyle
(74) *Attorney, Agent, or Firm* — troutman pepper locke; Tim Tingkang Xia, Esq.

(57) ABSTRACT

Provided herein are flexible, microfluidic epidermal systems and methods useful in the analysis of biofluids for biomarkers corresponding to a variety of conditions and methods of use. The provided systems configured to create conformal contact with the skin to allow for medical testing or screening, either in situ or later external laboratory testing. The described devices and methods may be used for cystic
(Continued)

fibrosis screening, glucose monitoring, drug and/or alcohol testing, creatinine monitoring, urea monitoring, pH measurement and dialysis treatment efficacy testing.

29 Claims, 16 Drawing Sheets

(51) Int. Cl.
    *A61B 5/103*     (2006.01)
    *A61B 5/145*     (2006.01)
    *A61B 5/1477*     (2006.01)
    *B01L 3/00*     (2006.01)
    *G01N 33/52*     (2006.01)
    *G01N 33/98*     (2006.01)

(52) U.S. Cl.
    CPC ...... *A61B 5/14532* (2013.01); *A61B 5/14539* (2013.01); *A61B 5/14546* (2013.01); *A61B 5/1477* (2013.01); *A61B 5/4842* (2013.01); *A61B 5/4845* (2013.01); *A61B 5/4848* (2013.01); *A61B 5/6832* (2013.01); *B01L 3/502715* (2013.01); *G01N 33/52* (2013.01); *G01N 33/98* (2013.01); *B01L 2200/16* (2013.01); *B01L 2300/023* (2013.01); *B01L 2300/027* (2013.01); *B01L 2300/047* (2013.01); *B01L 2300/0645* (2013.01); *B01L 2300/0803* (2013.01); *B01L 2300/123* (2013.01)

(58) Field of Classification Search
    CPC ............ A61B 5/14539; A61B 5/14546; A61B 5/1477; A61B 5/4842; A61B 5/4845; A61B 5/4848; A61B 5/6832; A61B 10/0096; A61B 2010/0006; A61B 2010/0009; A61B 2560/0412; A61B 2562/0295; A61B 2562/164; A61B 10/0064; A61B 5/14517; A61B 5/14521; B01L 3/502715; B01L 2200/16; B01L 2300/023; B01L 2300/027; B01L 2300/047; B01L 2300/0645; B01L 2300/0803; B01L 2300/123; B01L 2200/10; B01L 2300/0654; B01L 2300/0887; B01L 2400/0406; G01N 33/52; G01N 33/98; G01N 33/84; G01N 2800/382; A61F 2007/0067; A61M 2202/092
See application file for complete search history.

(56) References Cited

U.S. PATENT DOCUMENTS

| | | | |
|---|---|---|---|
| 2005/0106713 A1* | 5/2005 | Phan | G01N 33/528 702/19 |
| 2005/0180882 A1* | 8/2005 | Tung | A61B 10/0045 422/504 |
| 2006/0253011 A1 | 11/2006 | Edmonson et al. | |
| 2006/0275852 A1* | 12/2006 | Montagu | B01L 3/50273 435/7.93 |
| 2007/0027383 A1* | 2/2007 | Peyser | G01N 33/66 600/362 |
| 2007/0179371 A1 | 8/2007 | Peyser et al. | |
| 2007/0278097 A1 | 12/2007 | Bhullar et al. | |
| 2009/0299156 A1* | 12/2009 | Simpson | A61B 5/0002 600/301 |
| 2010/0063372 A1* | 3/2010 | Potts | A61B 5/14521 600/346 |
| 2010/0179403 A1 | 7/2010 | Martinsen et al. | |
| 2012/0083711 A1* | 4/2012 | Goldstein | A61B 5/4848 600/573 |
| 2012/0244529 A1* | 9/2012 | Fuchs | B01L 3/5027 435/7.1 |
| 2012/0258467 A1* | 10/2012 | Chinnayelka | G01N 33/52 435/7.1 |
| 2016/0262670 A1* | 9/2016 | Wasson | A61B 5/0033 |
| 2017/0296114 A1* | 10/2017 | Ghaffari | A61B 5/4266 |
| 2017/0370951 A1* | 12/2017 | Buffiere | G01N 33/54373 |

FOREIGN PATENT DOCUMENTS

| | | | | |
|---|---|---|---|---|
| WO | 2009025698 A1 | 2/2009 | | |
| WO | 2010030609 A1 | 3/2010 | | |
| WO | WO-2015066459 A1 * | 5/2015 | ......... | A61B 10/0064 |
| WO | 2016025430 A1 | 2/2016 | | |
| WO | 2016025438 A1 | 2/2016 | | |
| WO | WO-2016025468 A2 * | 2/2016 | ............. | A61B 5/002 |
| WO | 2017218878 A1 | 12/2017 | | |

OTHER PUBLICATIONS

Choi et al., Thin, Soft, Skin-Mounted Microfluidic Networks with Capillary Bursting Valves for Chrono-Sampling of Sweat, Advanced Healthcare Materials, 2017.
United States Patent and Trademark Office (ISR/US) "International Search Report for PCT/US2018/035674", US, Aug. 23, 2018.
EPO, "Supplementary Partial European Search Report for EP Application No. 18809259.7", Munich, Germany, Mar. 18, 2021.
JPO, "First Office Action for JP Application No. 2019-566267", Japan, Mar. 22, 2021.

* cited by examiner

Epifluidic Sensor

Medical-grade silicone and thin dimensions enables soft, flexible, intimate contact with skin

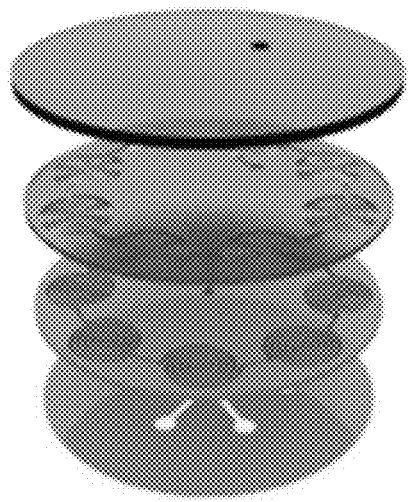

→ Capping layer — Sweat removed through direct pipette extraction

→ Analytic — Collection and on-device analysis microfluidic channel network

→ Adhersive — Skin-safe adhesive for conformal, air/water-tight skin seal

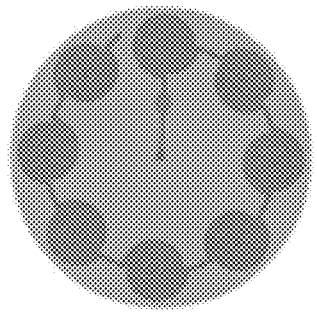

Each well stores 5 uL of sweat

Provides clear volume measurement in clinic

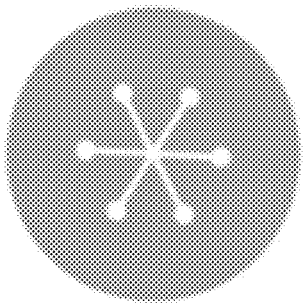

Patterned adhesive layer to structure flow of sweat into device

Flow results from sweat gland pressure

FIG. 3

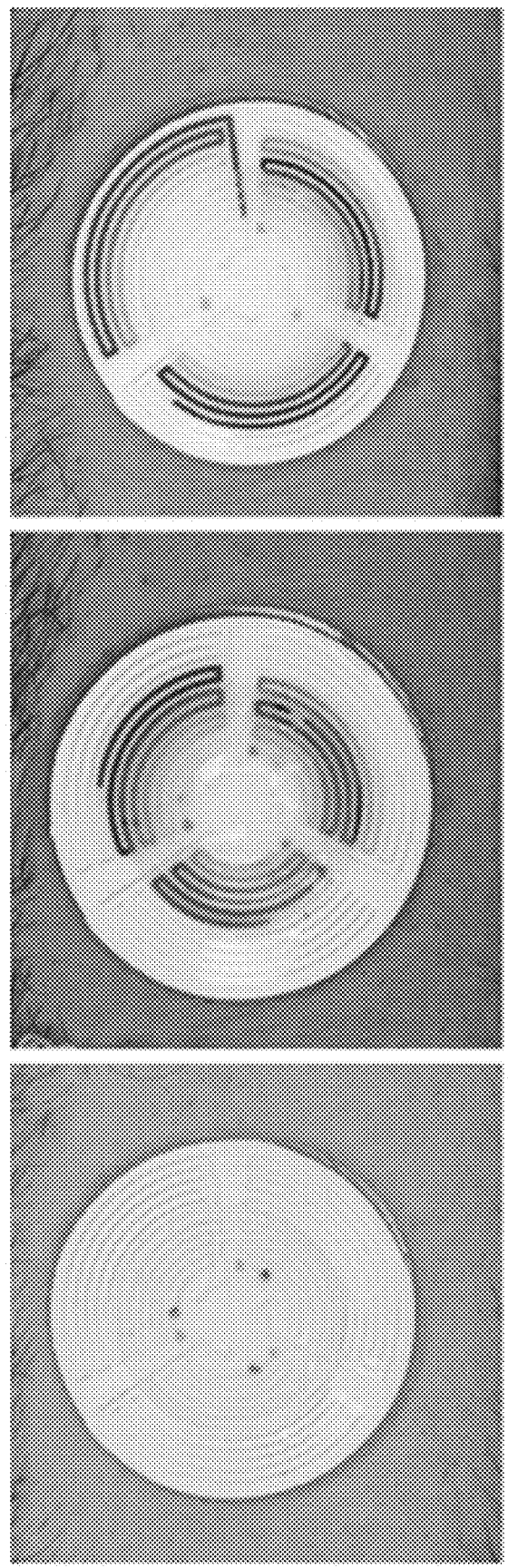
FIG. 6A  0 min
FIG. 6B  15 min
FIG. 6C  30 min

THIN, SOFT, SKIN-MOUNTED MICROFLUIDIC NETWORKS FOR DETECTION AND ANALYSIS OF TARGETS OF INTEREST IN SWEAT

CROSS-REFERENCE TO RELATED APPLICATIONS

This application claims the benefit of priority to U.S. Provisional Patent Application No. 62/514,515 filed on Jun. 2, 2017, which is specifically incorporated by reference to the extent not inconsistent herewith.

BACKGROUND OF INVENTION

Microfluidics provides a versatile technology platform impacting a wide range of industries and commercial products. In the field of medical diagnostics, for example, microfluidics has been essential to the development of entirely new classes of sensors and assays with potential for revolutionizing medical diagnosis and the treatment of disease. Lab on a chip and microarray systems, for example, have been developed for clinical pathology taking advantage of microfluidic sample collection, preparation and handling to achieve highly sensitivity and rapid point of care analysis of biomarkers in minute quantities of biofluid. The advances in microfluidics have also been leveraged to support other biotechnology and medical applications including high throughput DNA sequencing, mass spectrometry-based proteomics, cellular expression and imaging.

Wearable systems are another technology for which advances in microfluidics has potential to enable new classes of products and advanced modes of functionality. Recent developments in epidermal electronics, for example, provide a class of skin-mounted sensors and actuators compatible with efficient microfluidic sampling at the interface of the skin. Such microfluidics-enabled epidermal systems have potential to support a broad range of clinical applications in healthcare including analysis of biomarkers, drug administration, and real time diagnosis and monitoring of medical conditions including diabetes, inflammation and hydration state. [see, e.g., US20060253011; US20100179403; WO 2016/025468; WO 2016/025438; WO2010030609; US20070027383; US20070179371A1; U.S. Pat. Nos. 4,960,467; 6,198,953; and WO2009025698A1].

As will be understood from the forgoing, the development of wearable systems is needed integrating microfluidic functionality with specific and selective analytes in sweat. Wearable systems are needed, for example, having physical formats and mechanical properties providing a robust interface with the skin to achieve quantitatively reliable collection and handling of biofluids over clinically relevant time intervals. In addition, microfluidic systems are needed that are capable of effective collection, pretreatment, storage and analysis of biofluids to support a range of analyte testing using wearable systems.

SUMMARY OF THE INVENTION

Provided herein are flexible, microfluidic epidermal systems useful in the analysis of biofluids for biomarkers corresponding to a variety of conditions and methods of use. The provided systems configured to create conformal contact with the skin to allow for medical testing or screening, either in situ or later external laboratory testing. The described devices and methods may be used for cystic fibrosis screening, glucose monitoring, drug and/or alcohol testing, creatinine monitoring, urea monitoring, pH measurement and/or dialysis treatment efficacy testing.

The described systems are versatile and may use a variety of sensing or analyzing approaches alone or in combination, including, removal for later laboratory analysis, on device analyzers and/or colorimetric sensors. This may allow for the detection or quantification of a plurality of biomarkers by a single device or system.

In an aspect, provided is a method for the detection of a biomarker in sweat comprising: a) providing an epidermal microfluidic device to a skin of a subject, wherein conformal contact is established thereby providing fluidic communication between the device and the skin, the device comprising: i) a flexible substrate; ii) a sweat inlet embedded in or supported by the functional substrate; and iii) a reservoir chamber fluidically connected to the sweat inlet; b) collecting the sweat from the subject in the device; c) identifying or quantifying the amount of one or more biomarkers in the sweat; d) measuring the volume of said sweat collected or the flow rate of said sweat from said subject; wherein said one or more biomarkers are for i) monitoring or screening for cystic fibrosis, ii) monitoring drug or alcohol consumption, iii) monitoring dialysis efficacy, iv) monitoring glucose levels, v) monitoring creatinine levels, vi) monitoring urea levels, vii) monitoring pH or any combination thereof.

In an aspect, provided is a method for the detection of a biomarker in sweat comprising: i) providing an epidermal microfluidic device to a skin of a subject, wherein conformal contact is established thereby providing fluidic communication between said device and said skin, said device comprising: a) a flexible substrate; b) a sweat inlet embedded in or supported by said flexible substrate; and c) a reservoir chamber fluidically connected to the sweat inlet; ii) collecting said sweat from said subject in said device; iii) identifying or quantifying the amount of one or more biomarkers in said sweat as a function of time; and iv) measuring the volume of said sweat collected or the flow rate of said sweat from said subject; v) monitoring a health condition of said subject based on the one or more biomarkers in said sweat.

In an aspect, provided is a method for the detection of a biomarker in sweat comprising: i) providing an epidermal microfluidic device to a skin of a subject, wherein conformal contact is established thereby providing fluidic communication between said device and said skin, said device comprising: a) a flexible substrate; b) a sweat inlet embedded in or supported by said flexible substrate; and c) a first reservoir chamber having at least one colorimetric sensor, wherein said reservoir chamber is fluidically connected to the sweat inlet; d) a second reservoir chamber operably connected to an analyzer; ii) collecting said sweat from said subject in said device; iii) identifying or quantifying the amount of at least two biomarkers in said sweat, wherein each of said biomarkers are identified or quantified in a unique reservoir chamber; and iv) monitoring a healthcare condition of said subject based on at least two biomarkers in said sweat.

The device may further comprise an analyzer integrated with or fluidically connected to the reservoir chamber. The step of identifying or quantifying the amount of one or more biomarkers may be performed in situ using the epidermal, microfluidic device. The device may further comprise a sweat outlet fluidically connected to the reservoir chamber and the method may further comprise a step of removing the sweat from the device through the sweat outlet. The step of identifying or quantifying the amount or one or more biomarkers may be external laboratory based.

The flexible substrate may comprise a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, chitosan, and any combination thereof.

The device may further comprise an adhesive layer, wherein the adhesive layer comprises a second auxiliary in fluidic communication with the sweat inlet. The adhesive layer may be capable of reversibly adhering to the skin surface. The adhesive layer may comprise medical grade acrylic, silicone, or hydrocolloid.

The biomarker may correspond to cystic fibrosis. The biomarker may be a chloride. The biomarker may correspond to the presence or absence of alcohol and/or an illicit drug, for example, marijuana, cocaine, heroin, lysergic acid diethylamide (LSD), psilocybin, methamphetamine, ketamine or a combination thereof. The biomarker may be glucose. The biomarker may correspond to kidney or dialysis efficiency. The biomarker may be creatinine. The biomarker may be urea. The biomarker may be pH. The epidermal microfluidic device may have a plurality of reservoirs and each reservoir is used to identify or quantify a different biomarker.

The epidermal microfluidic system may further comprise a colorimetric sensor or a plurality of colorimetric sensors. The colorimetric sensor may be a dye and said dye provides a visual representation of the amount of sweat collected by said epidermal microfluidic device. Each of the colorimetric sensors may comprise one or more color-responsive reagents for quantification of a sweat volume or amount, flow rate, composition or any combination of thereof. Each of the colorimetric sensors may comprise one or more color-responsive reagents for quantification of chloride, glucose, alcohol, an illicit drug, urea, creatinine or pH.

The one or more color-responsive reagents may be indicator reagents that react with one or more biomarkers. The epidermal microfluidic device may comprises plurality of reservoir chambers, each of which having one or more color-responsive reagents and each of said color-responsive reagents are immobilized in a respective reservoir of the plurality of chamber reservoirs.

The one or more color-responsive reagents may be selected from the group consisting of dye, $CoCl_2$, glucose oxidase, peroxidase, potassium iodide, lactate dehydrogenase, diaphorase, formazan dyes, 2,4,6-tris(2-pyridiyl)-s-triazine (TPTZ) complexed with mercury ion or iron ion, a 2,2'-bicinchoninic acid, 1,10-phenanthroline, a universal pH indicator, silver chloranilate, and any combination thereof. The epidermal microfluidic device may have one or more color calibration markers. The epidermal microfluidic device may comprise further ion-selective electrodes and/or electrochemical sensors.

The epidermal microfluidic device may further comprise a temperature sensor, for example, a temperature sensor is embedded in or supported by said flexible substrate that provides a body temperature of said subject. The epidermal microfluidic device may further comprise a wireless device, for example, a transmitter, a receiver, both a transmitter and receiver, an NFC coil. The wireless device may be wirelessly powered. The wireless device may further comprise at least one LED, that may notify said subject when collection of said sweat is complete or when said epidermal microfluidic system is full of said sweat or notify the subject when quantification or identification of said biomarker is complete.

The subject may be a human subject, for example, a human subject undergoing a diagnostic procedure, undergoing a therapeutic procedure, monitoring the presence, onset or progression of a disease condition, or undergoing a fitness activity. Monitoring a health condition may comprise monitoring a condition or disease, monitoring the efficacy of a treatment, monitoring the effect of a therapy or monitoring a physical condition.

In an aspect, provided is an epidermal microfluidic system for collection of sweat from the skin of a subject, said device comprising: i) a flexible substrate; ii) a sweat inlet embedded in or supported by said flexible substrate; iii) at least one reservoir chamber fluidically connected to the sweat inlet; and iv) a microfluidic outlet fluidically connected to said reservoir chamber configured to allow removal of said sweat from said microfluidic system for external laboratory based biomarker analysis; wherein said microfluidic system is capable of establishing conformal contact with a skin surface of a subject.

In an aspect, provided is an epidermal microfluidic system for analysis of sweat from the skin of a subject, said device comprising: a flexible substrate; a sweat inlet embedded in or supported by said flexible substrate; at least one reservoir chamber fluidically connected to the sweat inlet; and an analyzer operably connected to said reservoir chamber and configured to analyze said sweat for one or more biomarkers; wherein said analyzer comprises one or more active components selected from the groups consisting of a photodiode, a laser diode, a vertical cavity surface-emitting laser, a waveguide, and an optical resonance cavity; wherein said microfluidic system is capable of establishing conformal contact with a skin surface of a subject.

In an aspect, provided is an epidermal microfluidic system for analysis of sweat from the skin of a subject, said device comprising: a flexible substrate; a sweat inlet embedded in or supported by said flexible substrate; a plurality of reservoir chambers fluidically connected to the sweat inlet; wherein each of said plurality of reservoir chambers independently has a microfluidic outlet fluidically connected to said reservoir chamber configured to allow removal of said sweat, an analyzer operably connected to said reservoir chamber or a colorimetric sensor; wherein said microfluidic system is capable of establishing conformal contact with a skin surface of a subject.

The laboratory based biomarker analysis, said analyzer and said colorimetric sensor may determine the presence or absence of a biomarker. The laboratory based biomarker analysis, said analyzer and said colorimetric sensor may quantify a biomarker.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 3 provides an example of an epifluidic device that allows the amount of sweat and the collection rate into the device to be modified or "tuned" by creating prescribed patterns in the adhesive or the skin/device interface layer.

FIG. 4 provides an example microfluidic device.

FIG. 5 provides an image of an example microfluidic device. FIG. 4A unaltered.

FIG. 6 provides an image of the device filling with sweat (colored) over a 30 min collection period after pilocarpine iontophoresis. FIG. 6A 0 min. FIG. 6B 15 min. FIG. 6C 30 min.

FIG. 7 shows the extraction of sweat from a device as described herein.

FIG. 8 provides an example of a soft and microfluidic device for colorimetric analysis of sweat.

FIG. 9 provides a schematic illustration of a device with color reference markers of pH, creatinine and urea.

FIG. 10 provides data regarding device performance as described in Example 4.

FIG. 11 provides an example of a colorimetric microfluidic device.

FIG. 12 provides data regarding device performance as described in Example 4.

DETAILED DESCRIPTION OF THE INVENTION

Figure 1:
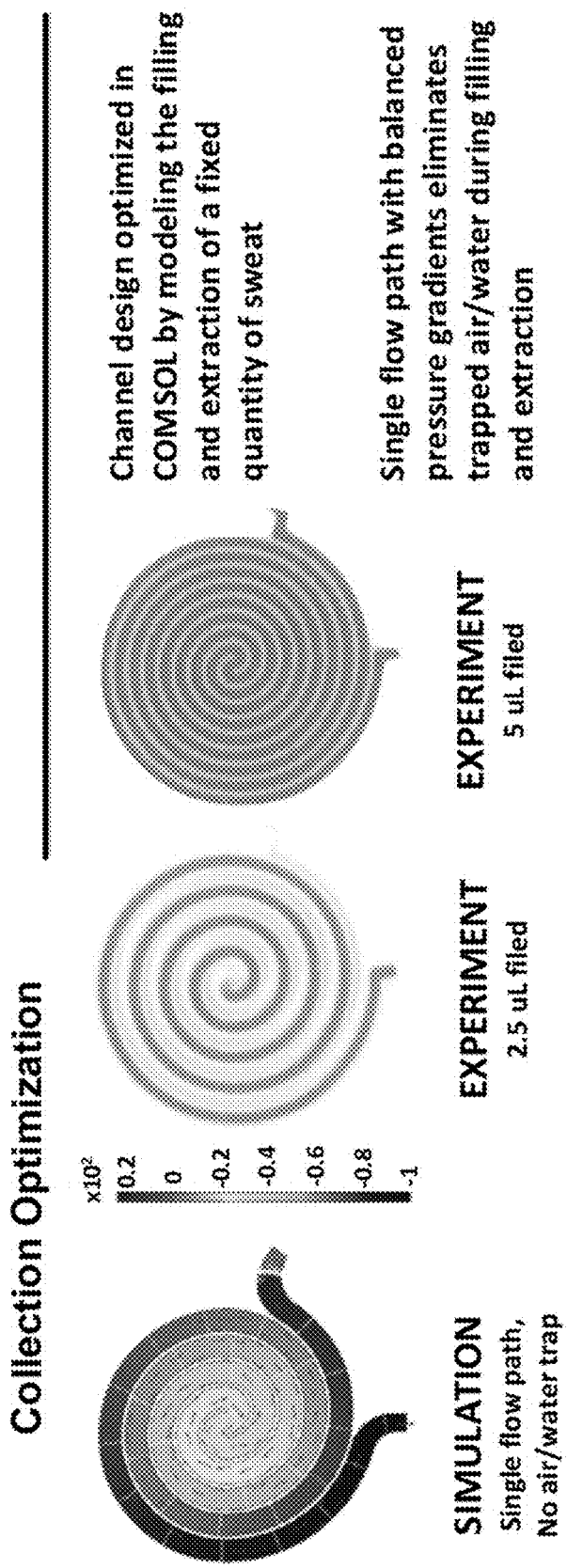
FIG. 1 provides an example of microfluidic networks optimized to be filled and to store biofluids in discrete amounts with approximately 100% efficiency.

In general, the terms and phrases used herein have their art-recognized meaning, which can be found by reference to standard texts, journal references and contexts known to those skilled in the art. The following definitions are provided to clarify their specific use in the context of the invention.

"Microfluidic device" refers to a system, device or device component containing liquid constrained in at least one physical dimension generally of the order of nanometers to millimeters, optionally nanometers to microns. Microfluidic devices may include structures for collecting, extracting, transporting, storing, analyzing and/or outputting fluids, including biofluids. In some embodiments, the liquid is constrained to a lateral dimension selected over the range of 1 nm and 1 cm, such as a lateral dimension (e.g., depth) selected over the range of 1 nm to 5 mm, 100 nm to 1000 µm or 500 nm to 100 µm, and a lateral dimension (e.g., width) selected over the range of 1 nm to 1 cm, 10 µm to 2 mm or 1 µm to 10 mm. In embodiments, an axial (e.g., flow) direction in a microfluidic system, device or device component can be long, for example on the order of meters, but will more commonly be 0.1 cm to 100 cm or 1 cm to 50 cm. Microfluidics are distinguished herein from macrofluidics. In some embodiments, the invention provides tissue mounted, optionally skin mounted, microfluidic devices. Microfluidic devices of some embodiments are capable of determining the composition of a biofluid such as sweat, for example, the presence, absence, and/or amount of one or more biomarkers, optionally as a function of time. Microfluidic devices of some embodiments are capable of determining one or more physical parameters characteristics of a biofluid, such as amount, volume, release rate and/or absorption rate, optionally as a function of time.

"Tissue-mounted" refers to systems, devices or device components having at least one surface capable of being supported, directly or indirectly, by a tissue surface, for example in a configuration providing fluidic communication and/or conformal contact. Epidermal systems and devices are a subset of tissue-mounted systems wherein the system, device or device component has at least one surface capable of being supported, directly or indirectly, by a surface of the skin, for example in a configuration providing fluidic communication and/or conformal contact. The invention provides tissue-mounted devices, such as epidermal systems, capable of collection, storage, treatment, processing, handling and/or analysis of biofluids such as sweat.

The expression "at least partially embedded in" refers to a configuration wherein an element, such as a microfluidic network or component thereof, is at least partially, and optionally wholly, integrated on or within a layer and/or device component, such as a substrate. In an embodiment, for example, "at least partially embedded in" refers to a configuration wherein an embedded element, such as a microfluidic element such as an inlet, outlet, passage, channel, and/or reservoir, at least partially comprises one or more surfaces, recessed features, relief features or any combination thereof, within or on a layer or device component it is at least partially embedded in. In an embodiment, for example, "at least partially embedded in" refers to a configuration wherein an embedded element, such as an inlet, outlet, passage, channel, and/or reservoir, at least partially comprises features molded or embossed on or into a layer or device component it is at least partially embedded in. In an embodiment, for example, "at least partially embedded in" refers to a configuration wherein an embedded element, such as an inlet, outlet, passage, channel, and/or reservoir, at least partially comprises features at least partially comprising surfaces (e.g., top, bottom, walls, etc.) of a layer or device component it is at least partially embedded. In an embodiment, for example, "at least partially embedded in" refers to a configuration wherein an embedded element, such as an inlet, outlet, passage, channel, and/or reservoir, is at least partially covered or encapsulated by another device component, such as a top layer or barrier layer.

"Substrate" refers to a device component, such as a layer, having a surface that is capable of supporting, accommodating, embedding or otherwise integrating a structure, including a microfluidic structure, optical structure, electronic structure, thermal structure or any combination of these. Substrates in some embodiments are capable of supporting, accommodating, embedding or otherwise integrating a device component such as microfluidic device component, optical device component, electronic device component, structural device component or any combination of these. In some embodiments, a substrate is capable of at least partially forming an interface with the tissue of a subject, such as with the epidermis or other organ of a subject. In an embodiment, a substrate of the present devices, systems and methods is a biocompatible and/or bioinert material. In an embodiment, a substrate of the present devices, systems and methods is a polymer or elastomer material. Substrates of the invention include "functional substrates" which refers to a substrate component for a device having at least one function or purpose in addition to providing mechanical support for a component(s) disposed on or within the substrate such as a microfluidic functionality, a mechanical functionality, optical functionality or a thermal functionality. A functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another. Devices and systems of the invention may have more than one substrate, for example, such as embodiments having a bottom substrate capable of establishing an interface with skin and an upper substrate layer, such as a barrier layer providing an interface with an ambient environment. For example, the invention includes devices and systems having a multilayer geometry including a substrate and barrier layer.

In some embodiments, a substrate is mechanically matched to a tissue, such as mechanically matched to skin. In an embodiment, a mechanically matched substrate is optionally capable of providing an interface for establishing fluid communication and/or conformal contact with a surface of the tissue, such as skin. Devices and methods of certain embodiments incorporate substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a desired contour profile, for example a contour profile allowing for conformal contact with a surface characterized by a surface topography comprising recessed and/or relief features. In certain embodiments, a desired contour profile is that of tissue, such as skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In some embodiments, devices of the invention are capable of establishing conformal contact with tissue of a subject, such as a portion of the skin of a subject.

"Sensing" refers to an action of detecting the presence, absence, amount, magnitude and/or intensity of one or more physical and/or chemical properties or characteristics. Sensor refers to a device or component thereof that is capable of sensing. Useful device components for sensing include, but are not limited to electrode elements, chemical or biological sensor elements, pH sensors, colorimetric sensors, electrochemical sensors, temperature sensors, strain sensors, mechanical sensors, position sensors, optical sensors and capacitive sensors.

"Actuating" refers to an action of acting on, stimulating, controlling, or otherwise affecting a structure, material or device component. Actuator refers to a device or component thereof that is capable of actuating. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. As used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 10000 microns, optionally less than 1000 microns and optionally less than 100 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, stretchable structures may also be flexible. Some stretchable structures (e.g., device components) are engineered to be able to undergo compression, elongation and/or twisting so as to be able to deform (and optionally operate) without fracturing. Stretchable structures include structures comprising stretchable materials, such as elastomers; and bent, coiled or serpentine structures capable of elongation, compression and/or twisting motion.

Devices of the present invention may optionally include one or more barrier layers. As used herein "barrier layer" refers to a device component spatially separating two or more other device components or spatially separating a device component from a structure, material, fluid or ambient environment external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid.

"Biofluid" refers to fluid generated by, extracted from or otherwise derived from the tissue of a subject, such as an organ of a subject. Biofluids include sweat, tears, saliva, gingival crevicular fluid, interstitial fluid, blood and combinations thereof.

As used herein, the term "fluidically connected" refers to the configuration of two or more components such that a fluid (e.g., a gas or a liquid) is capable of transport, flowing and/or diffusing from one component to another component, without adversely impacting the functionality of each of the components. Components may be in fluid communication via one or more elements such as channels, valves, tubes, containment structures, reservoirs, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

The terms "electrical contact" and "electronic contact" refer to the ability of two or more materials and/or structures that are capable of transferring charge between them, such as in the form of the transfer of electrons or ions. The terms "electrical contact" and "electronic contact" may refer to a configuration of two or more components such that an electronic signal or charge carrier can be directly or indirectly transferred from one component to another. As used herein, the terms "electrical contact" and "electronic contact" include one way and two way electrical communication. In some embodiments, components in electrical contact or electronic contact are in indirect electrical communication wherein an electronic signal or charge carrier is indirectly transferred from one component to another via one or more intermediate structures, such as circuit elements, separating the components.

As used herein, the term "electrical load" may refer to voltage or current applied to electrodes, sensors or other device components. The term "electrical response" or "electrical parameter" may refer to a voltage, current, or impedance response of the electrodes or sensors to the electrical load. For example, applying a current between two electrodes (electrical load) may induce a voltage drop between the two electrodes (electrical response). The electrical load may be a DC or an AC load.

The term "BLE" refers to a Bluetooth low energy system.

The term "functionalized" may refer to modification of a material or layer surface to add chemical, physical, electrical, optical or electrochemical functionality. In an embodiment, biological molecules or reagents may be deposited onto an electrode in a process of forming an electrochemical sensor.

The term "wet environment" may refer to the system being in a high-humidity environment or being at least partially surrounded by a liquid. The term "high-humidity" refers to the relative humidity of the surroundings being >70%.

Figure 13:
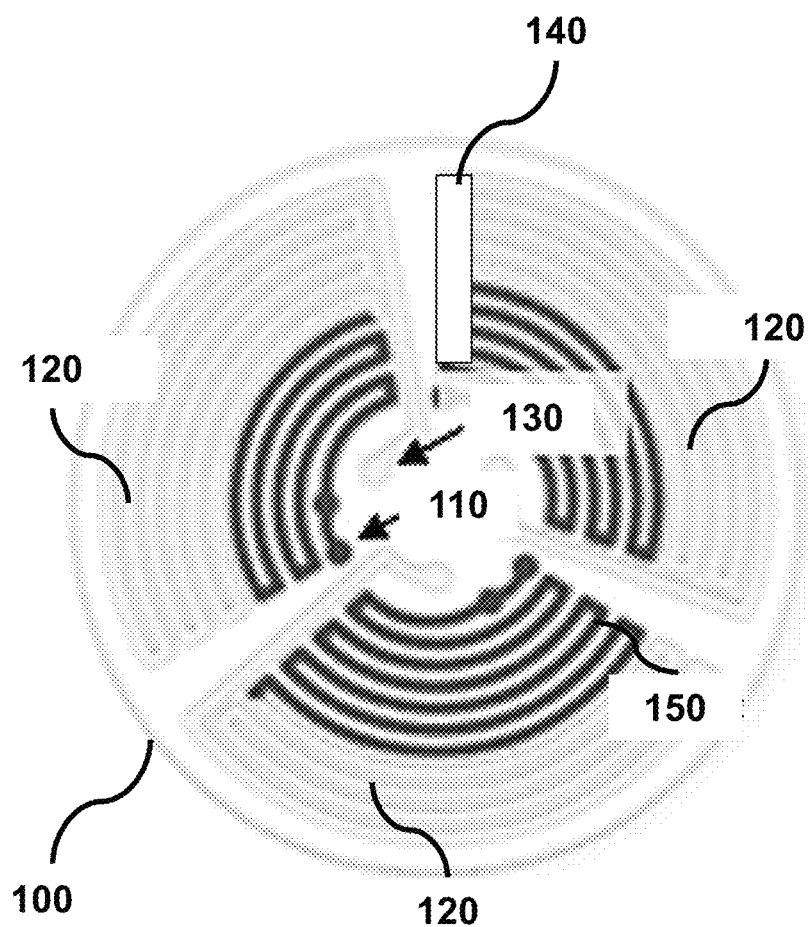
FIG. 13 provides a schematic of an example system, as described herein.

An example of an epidermal microfluidic system is provided in FIG. 13. One or more reservoir chambers 120 are provided in or on a flexible substrate 100. A sweat inlet 110 allows sweat to flow from the surface of subject through the flexible substrate 100 into the reservoir chamber 120. A sweat outlet 130 allows for the removal of sweat from the system, either from flow pressure or removed and collected to be later tested for the biomarkers described herein. There may be a single networked sweat inlet 110 or outlet 130 that is fluidically connected to each of the reservoir chambers 120 or a plurality of sweat inlets 110 or outlets 130, which each individually connect to a reservoir chamber 120. The reservoir chamber 120 may also be operably connected to an analyzer 140 and/or a colorimetric sensor 150 to provide in situ analysis or detection of biomarkers.

Example 1: Thin, Soft, Skin-Mounted Microfluidic Networks for Detection and Analysis of Targets of Interest in Sweat Abstract Described herein is a thin, soft, "skin-like" microfluidic platform is introduced that bonds to the skin to allow for collection and storage of sweat in an interconnected set of microreservoirs for the quantitative analysis of different targets of interest. Quantitative analysis can either be performed on the device or after collection via elution of sweat for external lab analysis. This platform is suitable for an array of applications including disease diagnostics through quantitative analysis of sweat chloride concentration for cystic fibrosis screening, monitoring of kidney health by measuring urea content in sweat, clinical and personal alcohol screening to quantify alcohol consumption, drug detection/screening, and personal/clinical glucose monitoring both continuously and at periodic time intervals. Each use case harnesses the soft, flexible mechanics, integrated sensors, and microfluidic handling of sweat to achieve precise, accurate, and quantitative measurements suitable for both clinical and personal health monitoring.

Applications

The provided systems and methods are useful for collecting and recovering biofluid such as sweat, blood from the epidermis for disease diagnosis, for example, by analyzing biomarkers in the biofluid. Additionally, the systems and methods are useful in collecting and analyzing organic and inorganic chemicals in sweat for home monitoring and self-quantification of conditions (e.g., drug screening, alcohol content monitoring).

Advantages

Provided is a single device for collecting sweat and analyzing biomarkers or other targets of interest. A self-adhesive is used to stick the device to the subject, so no additional skin-attachment assistance such as tourniquets or gauze. The device has a conformal, skin-compatible design for storage and final extraction of sweat. The device utilizes microfluidics to allow for analysis of small volumes of sweat. Further, the device may have a wireless connection to analytical components (smartphone, computer).

Brief Summary of Technology

Described are systems and methods for collection and storage of a liquid in a microfluidic channel network for either in situ or external, lab-based analysis. The device is in a soft, flexible configuration that enables conformal attachment to the epidermis promoting sweat collection while preventing loss. The device allows for the collection of either large or small volumes of sweat and performance of on-board analysis thereby enabling custom-tailored, rapid disease diagnosis and/or screening.

Technical Description

The described device is suitable for screening a wide array of targets of interest including biomarker concentration, such as chloride, for cystic fibrosis screening, organic/inorganic compounds for monitoring alcohol or drug consumption (such as marijuana), monitoring dialysis efficacy for patients with kidney failure (urea content in sweat), continuous (or discontinuous) monitoring of glucose levels in sweat, and other clinically/health relevant markers for disease screening, monitoring, and diagnosis.

The thin construction and soft mechanics of this device enables conformal attachment to the skin for the purpose of collecting, storing, and analyzing sweat. Overall, the device geometry may be both circular and rectangular in form. Radial geometries enable sweat extraction via centrifugation after the device is removed from the skin. Rectangular and radial geometries enable sweat extraction via pipetting or via a purpose-built extraction tool.

Figure 2:
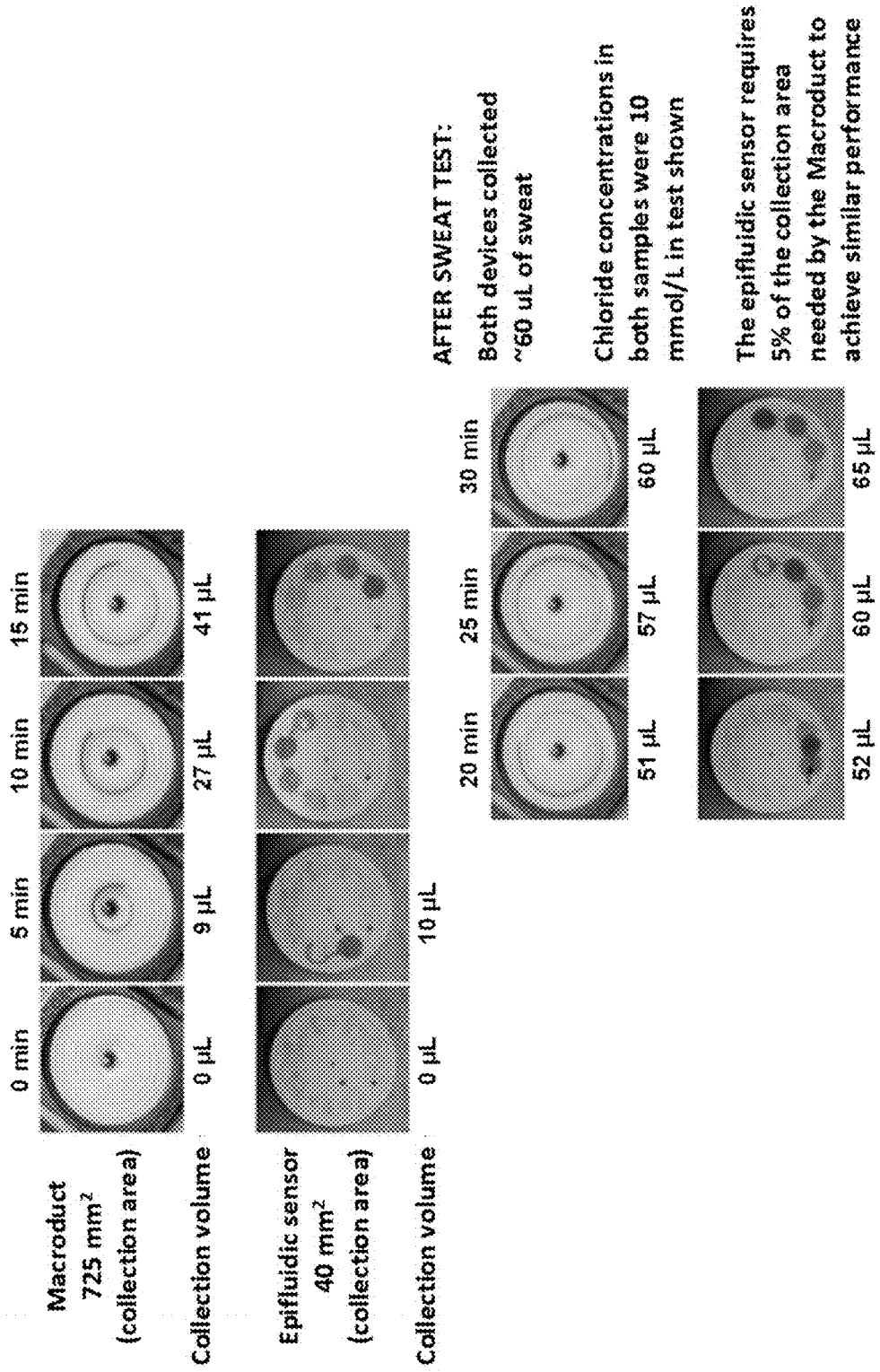
FIG. 2 illustrates that channels are designed so that they offer information about the current state of collection.

Advantageously, devices may be optimized for biofluid extraction. FIG. 1 illustrates microfluidic networks optimized to be filled and to store biofluids in discrete amounts without the trapping of air so that you can fully extract the biofluid with approximately 100% efficiency. Clinically it is advantageous to have a discrete volume of fluid, but, in some embodiments, a continuous channel for sweat storage with a visual design that provides the simulation of a "reservoir" to the human eye is implemented. The design is similar to a pipe designed to look like a bowl. While a bowl provides more visually apparent volume to a viewer, it may also trap air during filling or trap fluid during extraction. In contrast, in a pipe fluid flows easily but doesn't provide as clear visual volume information. The design utilizes both benefits by combining a pipe into a bowl shape for facile fluid filling or extraction without air entrapment while providing clear visual volume information. The benefit of this design is illustrated in FIG. 2. The channels are designed so that they offer information about the current state of collection. Fluid changes direction based upon a particular filling condition (¼ full, ½ full, of a target volume) providing have real-time, visual information about the current state of collection. Thus, the overall image of the device dynamically conveys information (e.g. visually).

Devices are fabricated from layers of poly(dimethylsiloxane) (PDMS) or other soft polymer supported upon either medical-grade acrylic adhesive film or on a custom spin-on adhesive composite for bonding to the skin. Materials used in device fabrication can be tailored for specific applications such as attachment to newborns, collection of volatile compounds, or long term drug monitoring (such as providing evidence of tampering with device). An exemplary multi-layer device is provided in FIG. 3. Further, in some devices, the device is epifluidic (e.g. controls the expose skin surface area to the device). This allows the amount of sweat and the collection rate into the device to be modified or "tuned" by creating prescribed patterns in the adhesive or the skin/device interface layer. Patterning allows optimized collection with maximum adhesion (see FIG. 3).

By controlling the skin surface area and thus collection area of the device, the efficiency and performance of the device is increased as compared to other collection methods (FIGS. 2 and 3). The same volume of sweat is collected in the same time, but with much less area exposed. This is due to the soft mechanics of the device, including flexible, conformal, and air/water tight sealed against the skin devices.

Devices are designed to extract specific volumes of sweat in a specified timeframe with particular embodiments fabricated with different fluidic channel widths, heights, and layouts. For a representative device, the first layer defines the microfluidic channel network (total thickness 400 µm). The second layer has no molded features and serves as the capping layer (thickness 200 µm) to the first layer to form enclosed channels. Both layers are fabricated from PDMS. The third layer forms the adhesive bond to the skin. Fluid (sweat) is routed into the device from the skin by way of an inlet formed by removal of the PDMS capping layer/adhesive layer. The diameter of the inlet determines how many sweat pores are sampled by the device.

Cystic Fibrosis

A sweat chloride test is the gold-standard diagnostic method used for screening cystic fibrosis whereby the quantitative analysis of the sweat chloride concentration is measured in microliter volumes of sweat captured from targeted collection sites on the skin by external laboratory methods. Current sweat test collection methods rely on either absorbent pads taped to the skin or a commercially available product; however, both methods are limited by ease of use, sample contamination, and poor sealing with the skin, especially when used for neonatal cystic fibrosis screening. A thin, soft, "skin-like" microfluidic platform that bonds to the skin is advantageous as it allows for collection and storage of sweat in an interconnected set of microreservoirs. Quantitative analysis can either be performed on the device or after collection via elution of sweat for external lab analysis.

A sweat sample captured via a sweat test is analyzed in a laboratory where coulometry is used to determine the concentration of chloride. While the foundational operation of the epifluidic device is the collection of sweat in a sweat test, quantitative chloride analysis can also be performed through integrated electrical sensors or via colorimetric analysis. By integrating ion-selective electrodes for chloride into the microfluidic network, electrochemical analysis of the chloride concentration can be performed in real-time as the sweat enters the device during elution. Using near-field communications, this data transfer and sensing can be conducted wirelessly. Furthermore, through continuous monitoring of the concentration, sweat rate can be measured and validated against the minimum sweat rate necessary for a valid cystic fibrosis test. As a result of the device flexibility, colorimetric analysis can also be performed either separately or simultaneously with electrochemical analysis to determine chloride concentration using commercially available colorimetric chemical assays.

Drug/Alcohol Screening

Devices for either acute or chronic drug screening are fabricated either for use in a clinical environment or as a temporary, at-home monitoring for analysis either by the wearer or by a clinician. Devices must be tamperproof if worn for home monitoring achieved via means such as destruction of sensitive components in the device itself (embedded art, fragile device construction in shear, broken indicator areas), staining of the skin with a colored dye, or electronic recording stored on the device so as to protect the integrity of the measurement. The same requirements are necessary for the clinic, but with a decreased need for long-term (~24 h) stability as tests are typically shorter (~10 min). Screening itself is achieved either via collection of sweat for external analysis, integrated electronic detection of key markers of drug/alcohol activity, via colorimetric analysis of key markers, or a combination thereof. Individual device barcoding will be required for drug screenings necessitated by legal requirements/chain of custody.

Devices for personal alcohol testing are fabricated in similar manner to other devices. Designed for personal use, these devices integrate graphics to provide clear, simple read-outs to accurately gauge alcohol consumption versus time. As aesthetics are important for use in a non-clinical setting the devices are designed to have as minimal a footprint as possible. Sensing is performed using either colorimetric or integrated electrode approaches. Key points of distinction are form factor, sampling volume, and chrono-sampling. Discrete monitoring is also possible via wireless sensing coupled with a smartphone.

Glucose Monitoring

Devices for glucose monitoring are fabricated in similar manner to other devices. Designed for both clinical and personal use, these devices integrate graphics to provide clear, simple read-outs to accurately gauge glucose over a specified time. Sensing is performed using either colorimetric or integrated electrode approaches depending upon measurement requirements. Key points of distinction are form factor, sampling volume, and chrono-sampling. Discrete monitoring is also possible via wireless sensing coupled with a smartphone.

Multilayer Device Construction

Multiple stacked microfluidic network device layers provide multifunctionality to the epifluidic sweat collection and analysis platform. Benefits include increased sweat storage in same epidermal surface area, independent collection areas for on-device controls, inclusion of active components (valving, electronic sensing), multiple analytical channels (electronic, colorimetric, external lab), and increased collection rates via multiple inlets. Multiple microfluidic network layers can be interwoven with graphical constructs to provide additional functionality by interacting dynamically with printed images.

Lensing

Integration of microlenses (e.g., cylindrical, hemi-spherical) into the microfluidic channel network can improve the accuracy of the colorimetric assay performance by either increasing the effect path length for light to pass through the device or by collecting more light scattered by the regions of interest (e.g., microfluidic channels). Additionally, integration of lenses into the device offer increased complexity for integration of art into the device such that the art can interact dynamically with the measurement in real-time.

Active Component/Nanoparticle Integration

To provide sensing capabilities, active components such as photodetectors, laser diodes, vertical cavity surface-emitting lasers (VCSEL), waveguides, optical resonance cavities can be integrated into the device. Additionally, device surfaces or composition can be modified to provide additional sensing capabilities through integration of plasmonic nanoparticles (e.g., gold nanorods) that respond to the presence of different analytes of interest. These components provide enhanced sensitivity to the described sensing requirements.

Fabrication Technique

Molds for fabricating these devices can be produced using standard cleanroom processing techniques, via refined additive manufacturing processes, or via micromilling. A molding process is used to produce accurate (~50 μm channel width) channels using 3D printing via stereolithography using photocurable resin. Mold production via micromilling aluminum also provides a method to rapid prototype molds with extremely fine resolution (~100 μm channel width, >30 μm depth).

A composite material comprised of soft-skin adhesive (e.g., Dow Corning) with uncured PDMS precursor is used to fabricate layers of soft polymer suitable for reversible bonding to virgin PDMS with a bond strength sufficient for a fluid-tight seal. Beneficially, neither heat nor oxygen plasma are required to form sealed, flexible, soft epifluidic devices. Furthermore, the reversible nature of the bond enables reusable device fixtures (e.g., electronics) with disposable fluidic networks. Formulations of different composite mixtures (30:1, 40:1, 50:1) provide different adhesive strength suitable for a variety of applications including bonding to electronic components and temporarily sealing channels for surface treatment/activation. Absence of surface plasma activation or heat treatment enables integration of sensitive assays (enzymes) or rapid prototyping while maintaining same surface chemistry.

Figure 4A:
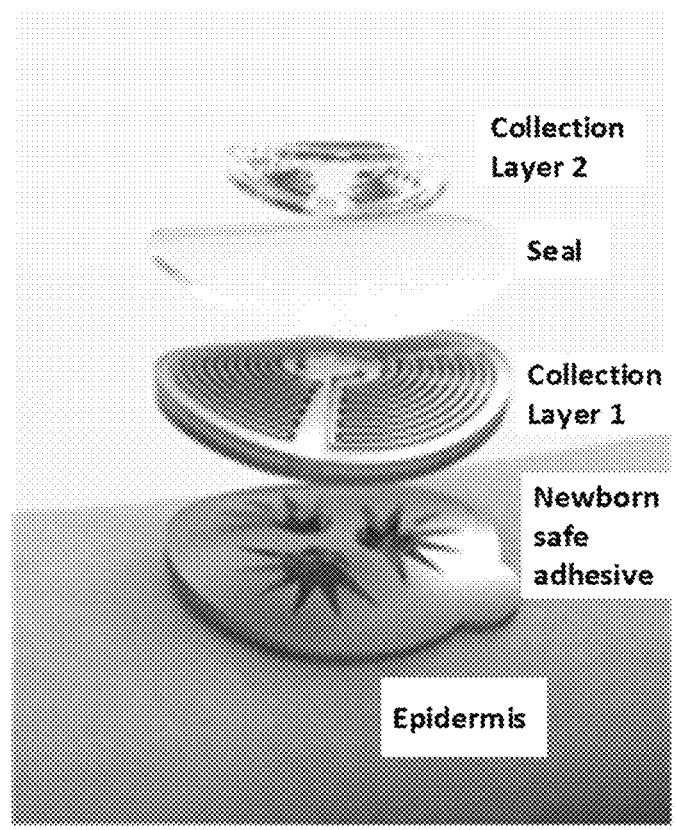
FIG. 4A Schematic of collection device.

Example 2: Thin, Soft, Skin-Mounted Microfluidic Networks for Detection and Analysis of Targets of Interest in Sweat: Optimization and Extraction We have demonstrated an analytical platform for the diagnosis of cystic fibrosis that exploits ultrasoft, conformal, "skin-like" microfluidic channels to collect sweat from eccrine sweat glands stimulated via pilocarpine iontophoresis. A representative device, shown in FIG. 4A, has an overall circular geometry with a diameter of 34 mm. The radial construction allows for both maximal sweat collection of a stimulated region (30 mm, diameter of Wescor® Pilodisc®) and attachment to multiple body locations (e.g., forearm, thigh) on multiple subjects (e.g., infants, adults).

Figure 4B:
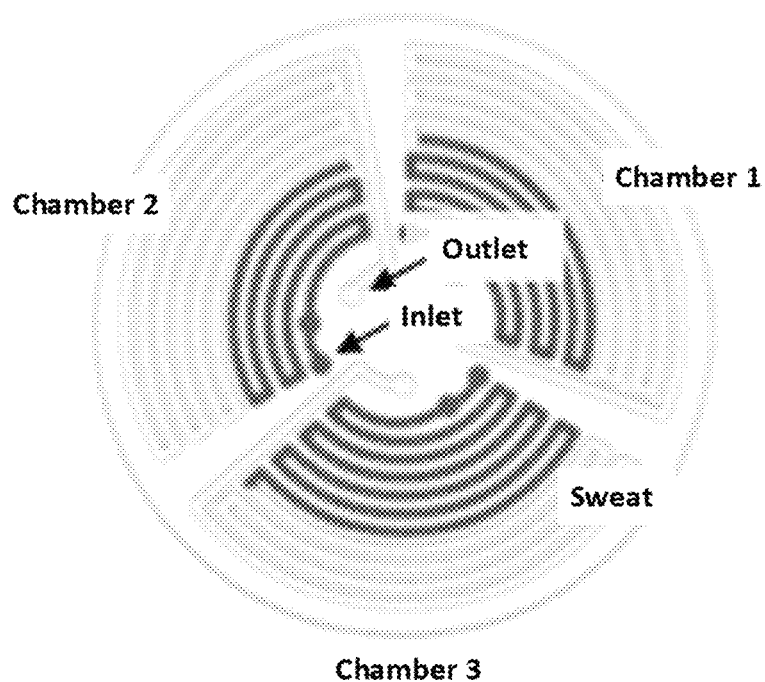
FIG. 4B the device collection layer (1) consists of three independent chambers, each with an inlet and outlet.

The device, comprised of three layers of soft, medical-grade silicone elastomer (polydimethylsiloxane, PDMS, Dow Corning) exploits thin geometries and soft mechanics to enable intimate, conformal bonding to fragile newborn skin. This bond is a zero-pressure, fluid-tight interface between the device and the skin formed via a medical-grade, irritation-free, FDA-approved gentle skin (i.e., newborn safe) adhesive (3M® silicone adhesive; thickness, 100 μm). Laser-patterned openings define the sweat harvesting regions through which sweat, driven by the sweat gland pressure (~3 kPa) passes into one of three independent chambers (FIG. 4B), which each store in excess of 70 μL of sweat. Optimization of the adhesive pattern maximizes sweat collection (70 mm² exposed surface area per region corresponding to ~100 sweat glands) while maintaining conformal adhesive contact during a sweat test.

Figures 5A, 5B, 5C:
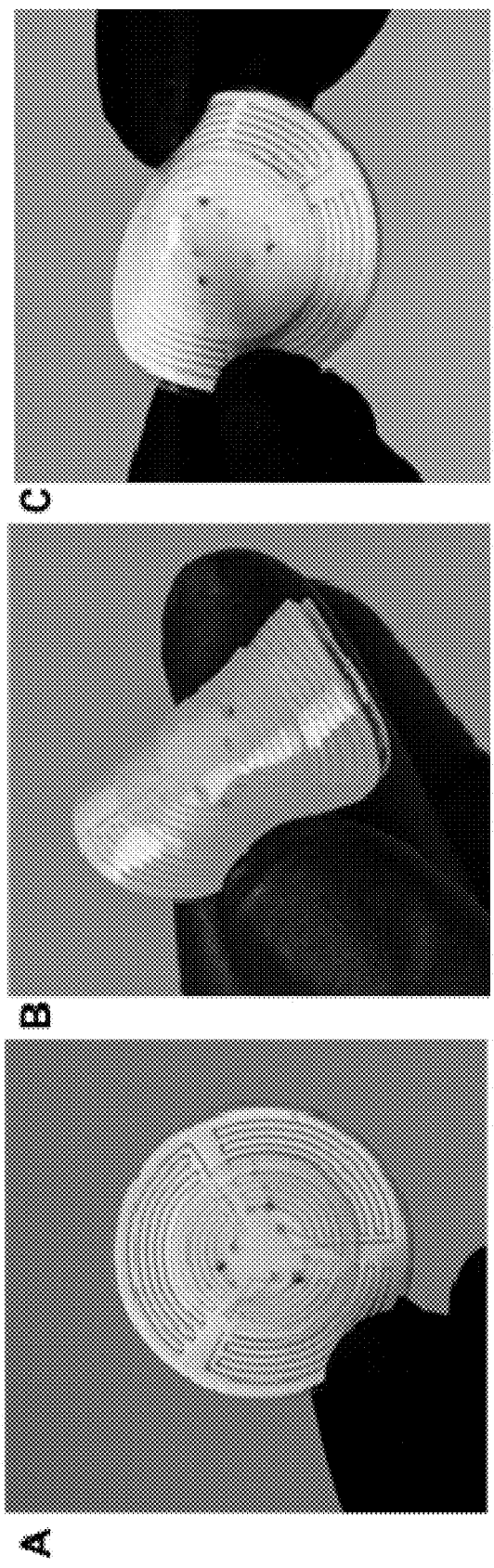
FIG. 5B undergoing bending.
FIG. 5C undergoing twisting.

The device consists of an embedded microfluidic network of embossed channels (500 μm width, 350 μm uniform depth) in a soft (~145 kPa) PDMS layer (thickness, 400 μm). A capping layer (thickness, 100 μm) serves to seal the first collection layer in which a single, continuous channel comprises a collection chamber with an inlet (open to skin) and an outlet to the second collection layer. This second layer contains embossed channels (500 μm width, 300 μm uniform depth) which form three secondary collection chambers connected to the first layer chambers by independent inlets. The middle capping layer also serves to seal the second layer microfluidic channel network. The first layer chambers each hold 50 μL of sweat while the second layer chambers each hold an additional 20 μL of sweat. Constructed in a tiered manner (first layer diameter, 34 mm; second layer diameter, 20 mm), the variable thickness of the device (edge thickness, 500 μm; center thickness, 900 μm), coupled with the soft material properties of the PDMS, improves device flexibility (FIG. 5). The thin, soft, compliant device construction provides a key differentiating factor between this device and the current FDA-approved technology (e.g., Macroduct® sweat collection system) as it enhances the conformal coupling to the skin, especially for neonates.

Figure 7C:
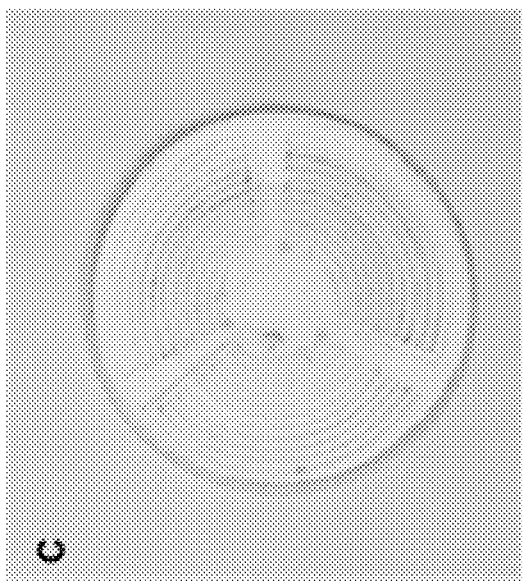
FIG. 7C Example device geometry optimized to fully extract sweat.
Figure 7B:
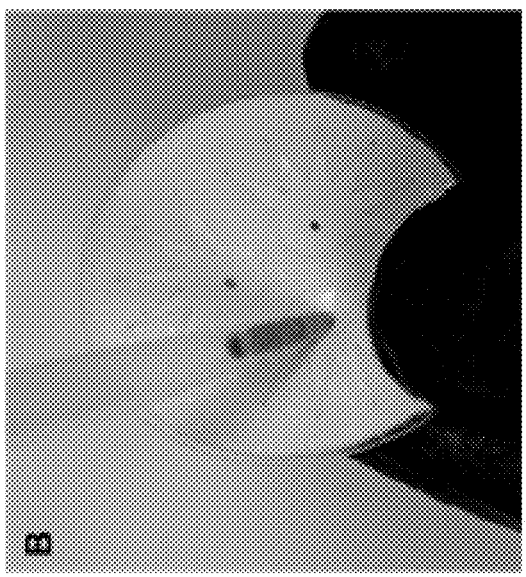
FIG. 7B Once removed from the skin, a standard pipette provides sufficient negative pressure to extract the sweat.
Figure 7A:
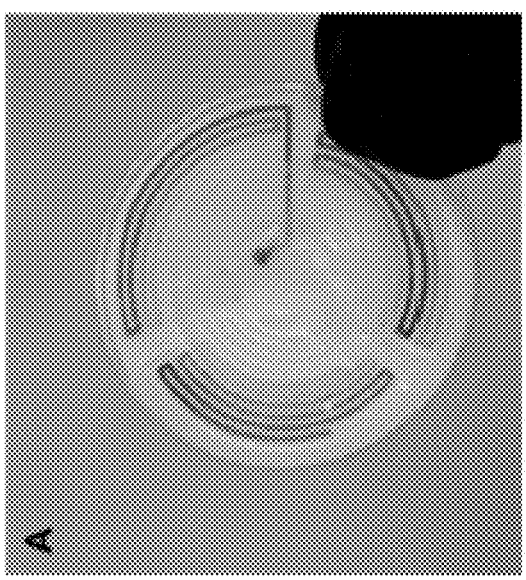
FIG. 7A device filled with sweat.

Optimization of the microfluidic channel design enables maximized sweat collection after pilocarpine iontophoresis. FIG. 7 shows a sequence of optical images of the device immediately after sweat stimulation, 15 min into the collection, and at the conclusion of a sweat test (30 min). The channels on the first layer contain reservoirs of teal dye (FDA approved, verified chloride-free) to visualize the flow of sweat as soon as sweat enters the device. As the device samples from three independent regions within the stimulation area, slight variations may result due to the biological variation of sweat gland density. The use of medical-grade soft skin adhesive provides a robust, water-tight bond between the device and skin promoting the complete and rapid collection of sweat without the application of a tourniquet. This eliminates a significant risk to neonates, especially when the diameter of the arm is smaller than the size of a Macroduct® sweat collection system device. As the adhesive layer provides an optimal balance between bond strength and sweat collection (evaluated by the absence of leakage), rather than high-pressure contact, the collection device does not suffer from motion-induced collection failures.

An additional design consideration of the collection device is the efficacy of sweat extraction and ease-of-extraction. Not only must sweat be fully extracted from the device, but the extraction mechanics must promote ease of operation and eliminate potential sources of chloride contamination. The location of the collection inlets (i.e., opening to skin) in the central region of the device (FIG. 4) eliminates sweat leakage upon the removal of the device from the skin as the mechanics of removal (i.e., vertical lifting from the device edge) creates a temporary pumping action to transport sweat contained in the channel farther into the collection chamber as observed in positional difference between the optical image in FIG. 6 (30 min) and that of FIG. 7A. The only additional equipment required to extract sweat from the collection device is a standard pipette (1 mL, generic). The device-layer inlet size (1.2 mm diameter) is smaller than the pipette opening (1.5±0.1 mm diameter, brand dependent) so that when the pipette contacts the elastomeric device a strong, temporary water-tight and gas-tight seal forms so that a negative pressure occurs in the microfluidic channel upon extraction with the pipette. This negative pressure is sufficient to fully extract sweat from each chamber, regardless of filled volume. The sweat extraction rate is linearly proportional to the amount of negative pressure applied (set volume on a variable pipetter) and rate of draw on the pipetter. The combination of extracted sweat from all three collection chambers defines the total collected sweat volume.

Figure 8A:
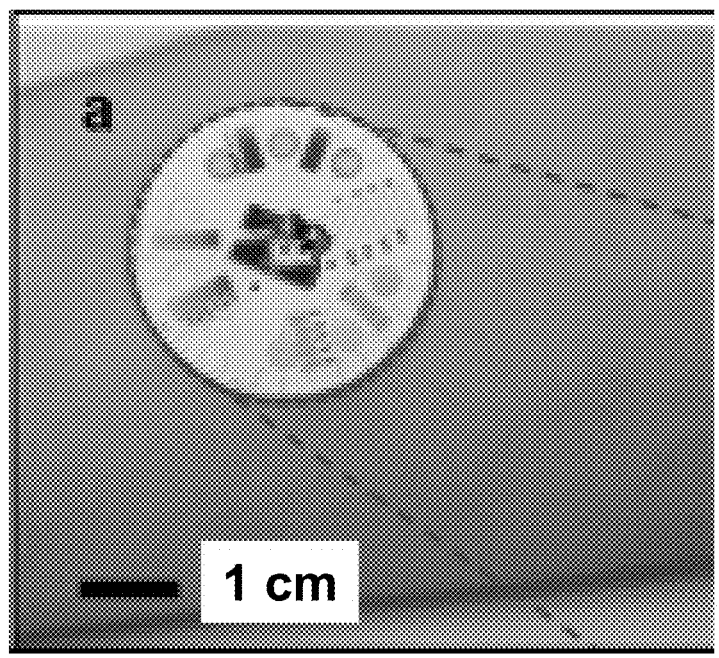
FIG. 8A shows a device on the skin of a subject.
Figure 8B:
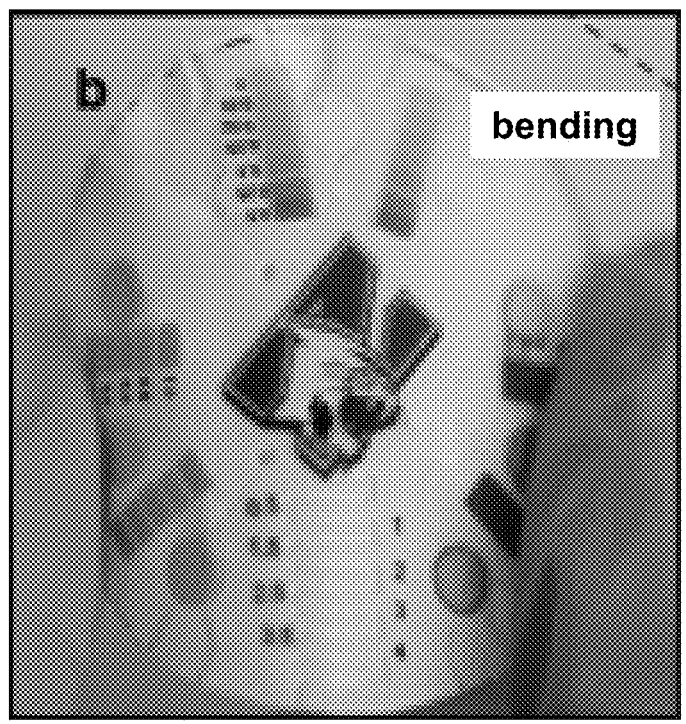
FIG. 8B shows a device under mechanical diction of bending.
Figure 8C:
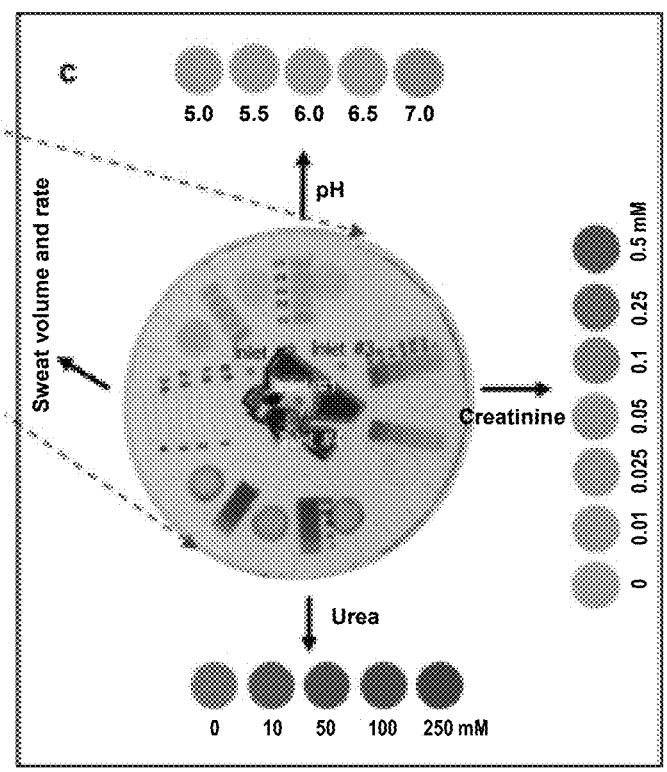
FIG. 8C is a top view illustration of a microfluidic device with colorimetric assays and reference marker.
Figure 8D:
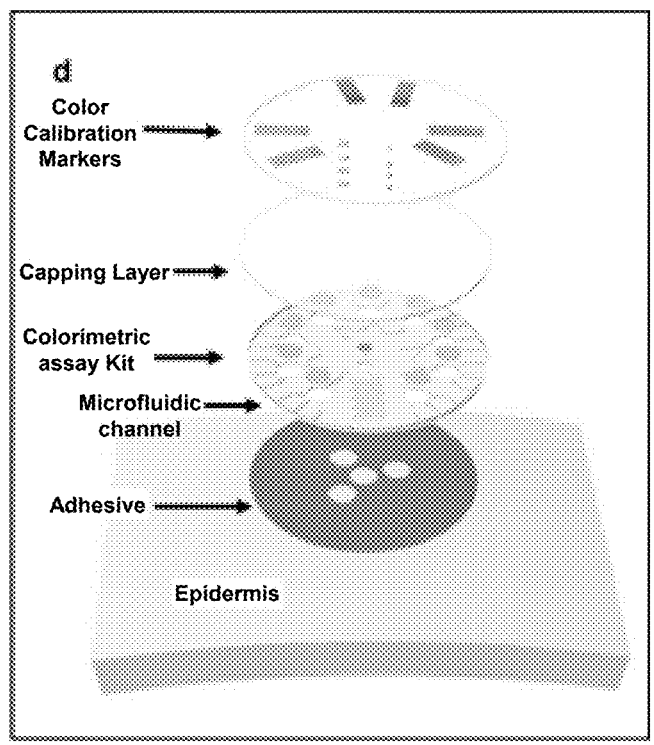
FIG. 8D is an exploded view illustration of a device and its interface with the skin.

Example 3: Soft, Multi-Functional Microfluidic Device for Colorimetric Analysis of Sweat Creatinine and Urea This example provides a soft microfluidic device made from PDMS has flexibility and interfaces to the skin (FIGS. 8A-B). The device provides several functionalities that: 1) analyzes the concentration of creatinine, urea, and pH in sweat, 2) calculates instantaneous sweat rate and local sweat loss via adhesive layer that provides a water-tight sealing between skin and the device that enables the device to collect sweat continuously (FIG. 8C). Sweat gland under open region of skin under adhesive generates sweat flow about 2 kPa to 1) inlet #1 fills the serpentine channel then shows sweat rate and the local sweat loss, 2) inlet #2, 3 and 4 fills the collection chambers in clockwise sequential manner through the guide of series of capillary bursting valves and develop color for the detection of pH, creatinine, and urea in sweat. For colorimetric analysis, each chamber has a chemical assay paper that develop color according to target biomarker in sweat and color reference markers placed next to the chamber to provide a standard color of target biomarker concentration for accurate color analysis that is not affected by light condition. The exploded view of the device shows the detailed compositions of one device (FIG. 8D). The adhesive layer attaches the PDMS device on to the skin and the hole in the adhesive opens a route for the sweat from the region to enter to the microfluidic channels. White microfluidic PDMS channel layer formed by soft lithography has four channels: the bottom serpentine channel for measuring sweat rate and local sweat loss, other circular chambers for measuring pH, creatinine, and urea concentration in sweat. The chemical assay components are placed in each chambers and channel for their purpose. A 200 μm thick clear 10:1 PDMS capping layer, treated with oxygen plasma to make it sticky, was placed onto microfluidic PDMS channel, to generate the closed channel. On top the capping layer, a 25 μm thick thin PET film with reference color marker provide an accurate color analysis.

Device Fabrication: Fabrication began with making a silicon wafer mold. Patterning photo-resist of KMPR 1010 (Microchem, MA, USA) on 1 mm thick Si-wafer and deep reactive ion etching (STS Pegasus ICP-DRIE; SPTS Technologies®, Newport, United Kingdom) generated a mold for microfluidic channels and reservoirs. Thin layer of poly (methylmethacrylate) (PMMA; Microchem®, MA, USA) formed on the mold as an anti-adhesion layer. Pouring 10:1 PDMS (Sylgard 184; Dow Corning®, MI, USA) mixed with white silicone dye (Reynolds Advanced Material, 5% wt) on the mold and spin coating at 200 rpm with baking at 70° C. for 45 min. Capping layer was spin coated with 10:1 PDMS at 200 rpm and baked at 70° C. for 45 min. Both microfluidic channel layer and capping layer were treated with laboratory corona treater (Electro-Technic Products) for better adhesion right before loading assays. All the chemical assays were located on the cured PDMS channel. 25 μm thick clear polyester film (THERMLfilm SELECT® 10852; FLEXcon, MA, USA) on the top of the device with color reference marker. 60 μm thick medical grade acrylate adhesive (1524; 3M, MN, USA) bonded to the bottom of the device with 30 sec of corona treatment.

Figures 9A, 9B:
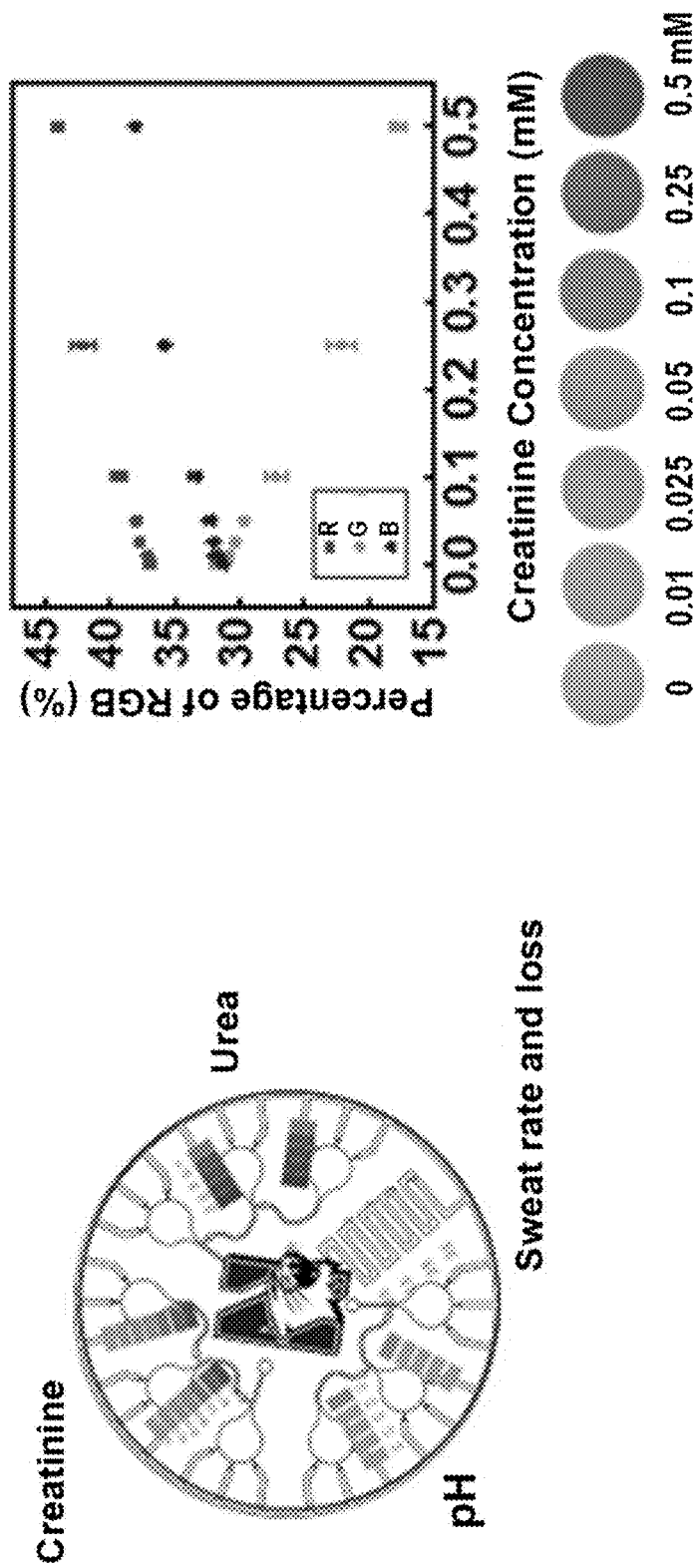
FIG. 9A shows an example device.
FIG. 9B creatinine.
Figure 9D:
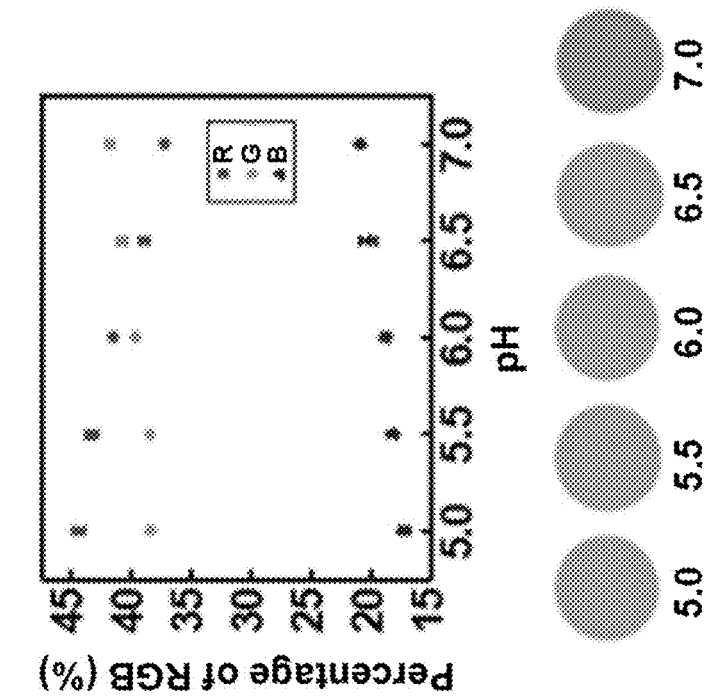
FIG. 9D pH. Color level of each concentration (top) and images of color development of assay chambers according to sample concentrations is shown in FIGS. 9B-D.
Figure 9C:
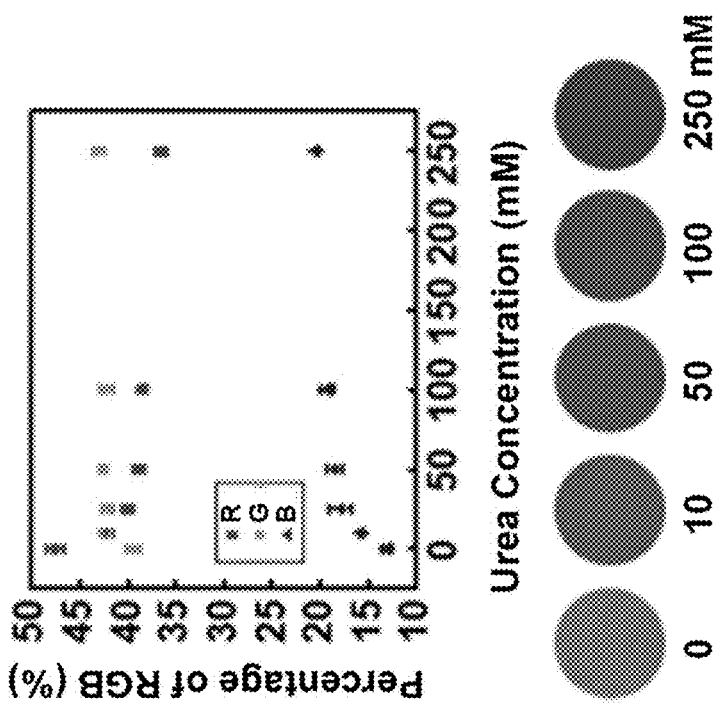
FIG. 9C urea.

Color development and reference marker: Colorimetric method for detection of biomarkers needs a color reference marker for accurate analysis of color regardless of light condition. FIG. 9A shows the collection of color reference markers for analyzing pH, creatinine, and urea from sweat. For the preparation of the color reference marker, in vitro test with standard solution produced reference color and digital imaging and image analysis provides color value of each assay. From the values, the color reference marker is generated and printed on the thin and clear film and attached to the top of the device. Creatinine in the sweat produces hydrogen peroxide ($H_2O_2$) from the enzymatic reaction with creatininase, creatinase, sarcosine oxidase, and peroxidase and reacts with probe using $H_2O_2$ results red color that changes green level in the chamber dominantly (FIG. 9B). Urease immobilized in pH paper decomposes urea in sweat into ammonia, changing the color of pH paper from yellow to green, where the red level changes dominantly with urea concentration (FIG. 9C). Universal pH dye provides a pH sensor and red level from the sensor that changes dominantly with pH of solution serve a comparing parameter of the color of assay (FIG. 9D).

Colorimetric Assay:
1) Urea: 0.01 mg/ml urease solution was prepared with urease (urease from Canavalia ensiformis, Jack bean, type III; Sigma-Aldrich®, MO, USA) in deionized water. Urea assay paper was prepared by immobilizing 2 μL of urease solution onto a pH paper (diameter, 3 mm, Hydrion Strips B 1-11, Micro Essential Laboratory®, NY, USA) and drying under vacuum in a desiccator for 15 min.
2) Creatinine: the creatinine assay solution was generated by fully mixing 24 μL of buffer, 8 μL of each enzyme solution, creatininase, creatinase, and enzyme mix, and 2 μL of probe. Creatinine assay paper was prepared by spotting 2 μL of cocktail solution onto a filter paper (diameter, 3 mm) and drying under vacuum in a desiccator for 15 min (Creatinine Assay Kit; Sigma-Aldrich®, MO, USA). A metal punch (diameter, 3 mm) was used to create circular pH papers for urea and filter papers for creatinine.
3) pH: pH cocktail solution was realized by thoroughly vortexing 4 mL of universal pH dye (Fisher Scientific®, NH, USA), 274 mg of polyvinyl chloride (M.W. ~233,000, Sigma-Aldrich, MO, USA), 635 μL of o-nitrophenyloctylether (Sigma-Aldrich®, MO, USA) and 508 μL of aliquot in 10 mL of tetrahydrofuran (Sigma-Aldrich®, MO, USA) till a homogenous suspension was obtained. Thereafter, a filter paper was dipped in the cocktail solution for 10 s and allowed to dry at ambient conditions for 15 min to realize the solid-state pH assay. Finally, a metal punch (diameter, 3 mm) was used to excise circular pads of the pH assay paper for incorporating in the wearable patch.

Standard color development and color reference marker preparation: Creatinine solution was prepared by dissolving creatinine from creatinine assay kit (Sigma-Aldrich®, MO, USA) in DI water. Urea (Sigma-Aldrich®, MO, USA) generated standard solutions in DI water as its concentrations. pH buffer solution was made by 1×PBS buffer (pH 7.4, Sigma-Aldrich®, MO, USA) and hydrochloric acid (37%, Sigma-Aldrich®, MO, USA), and pH meter (Mettler Toledo®, Greifensee, Switzerland) measured it. For creatinine, urea and pH test, pipetting 2 μL of standard solution into the chambers. For full color development, the device with creatinine and urea assay filled by the solution stayed in the oven at 37° C. for 15 min and pH for 5 min. A digital SLR camera (EOS 6D; Canon®, Tokyo, Japan) took the picture of the device. Photoshop (Adobe Systems®, CA, USA) provided color extraction from the color in the chambers. A color laser printer (C454 PS; Konica Minolta®, Tokyo, Japan) produced a reference maker on PET film at 1200 DPI resolution. The printed the reference marker placed on the device again and smartphone camera (Iphone 5s; Apple®, CA, USA) took picture of the chamber with reference marker. The color analysis compared the color level from the chamber and reference marker. Three spots from each chamber and reference marker provided the average color value. By adjusting brightness of the image, repetition of printing and comparing provided the optimum reference marker.

Figure 10A:
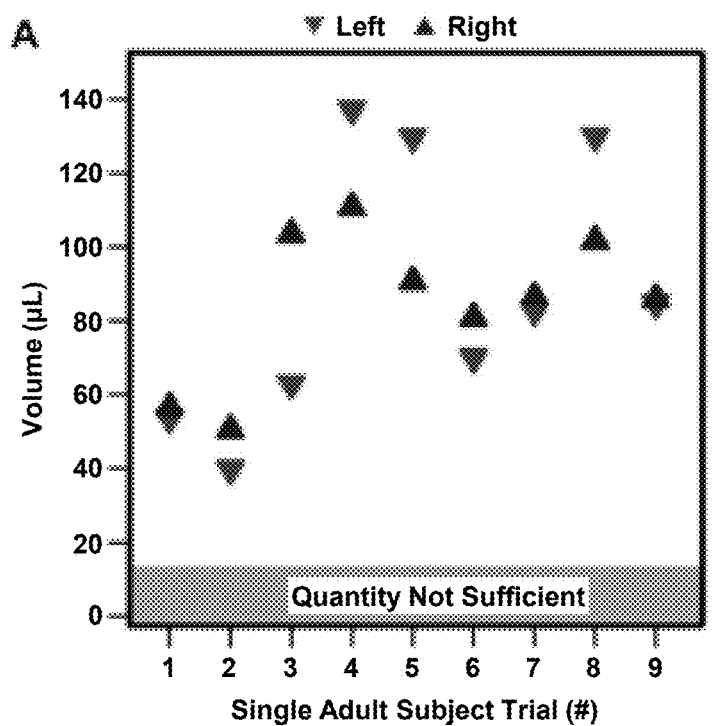
FIG. 10A Sweat collection volume for one adult volunteer over 9 days for both the left and right arms.
Figure 10B:
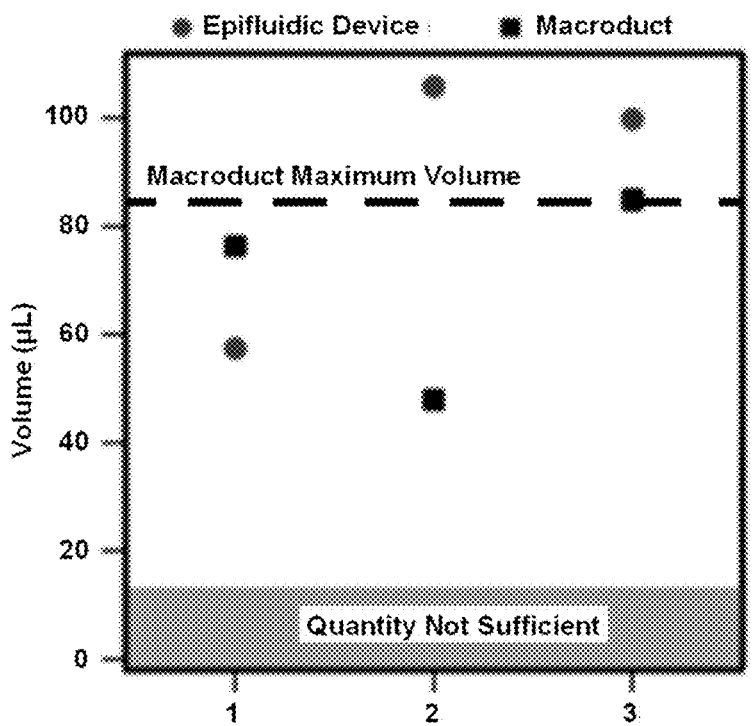
FIG. 10B Comparison of epifluidic device and Macroduct sweat collection volumes for three adult volunteers.
Figure 10C:
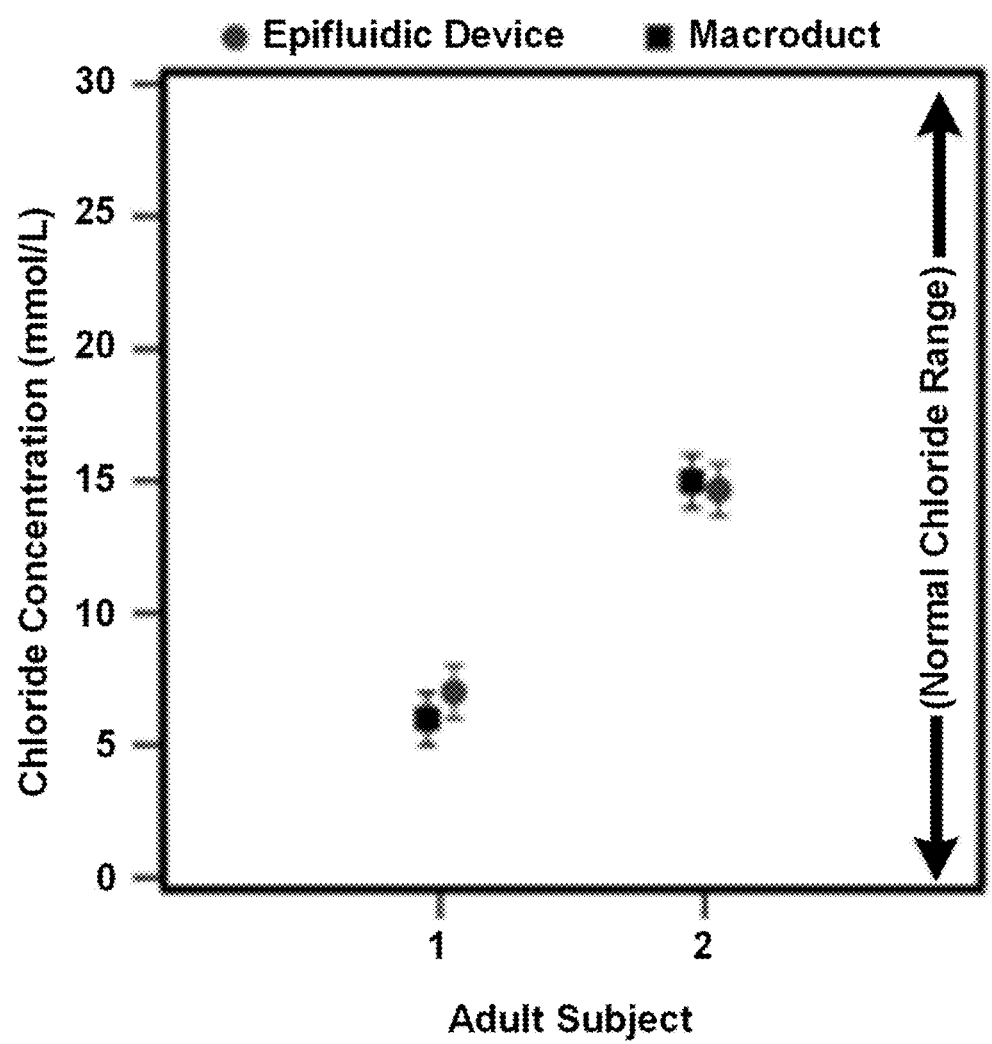
FIG. 10C Chloride concentration for collected sweat for two adult volunteers.

Example 4: Thin, Soft, Skin-Mounted Microfluidic Networks for Detection and Analysis of Targets of Interest in Sweat: Optimization and Extraction: Device Performance Device Performance: To test device performance in a laboratory setting, we conducted a study on a small (N=3) number of adult volunteers substituting our device for the Macroduct® sweat collection system. The study assessed the collection performance over a 9-day period with a variable hydration state (FIG. 10A), a contra-lateral study of the device efficacy vs. Macroduct device (FIG. 10B), and comparison of chloride values of collected sweat evaluated using the ChloroChek® (FIG. 10C). For all cases no QNS instances occurred. Over the 9-day volume study, the collection device demonstrated reproducible collection performance.

The exemplary epifluidic device collected at least 40 µL of sweat regardless of hydration state during the 30 min collection timeframe and for the majority of the study days sweat collected was in excess of 80 µL. Arm-to-arm variation was within expected ranges for iontophoretic stimulation (<35%). As shown in FIG. 10, an initial contra-lateral study between the Macroduct® and the collection device on three adult volunteers (same day) demonstrated performance equivalence. Variation observed for Subjects 1 and 3 is within the expected aforementioned range; however, the device collection volume for Subject 2 indicates the potential for enhanced collection performance.

Validation of the epifluidic collection device performance required verification of chloride level similarity between sweat obtained via the Macroduct® pilocarpine stimulation and collection device. FIG. 10C shows the chloridometer (ChloroChek®) measurements (N=5 runs) of each sweat sample from a single iontophoresis stimulation session (separate arms). The absence of variation between the measured values for the two subjects indicates that both the teal dye is chloride-free and no difference exists between the sweat collected via either method (beyond standard biological variation).

Figure 11B:
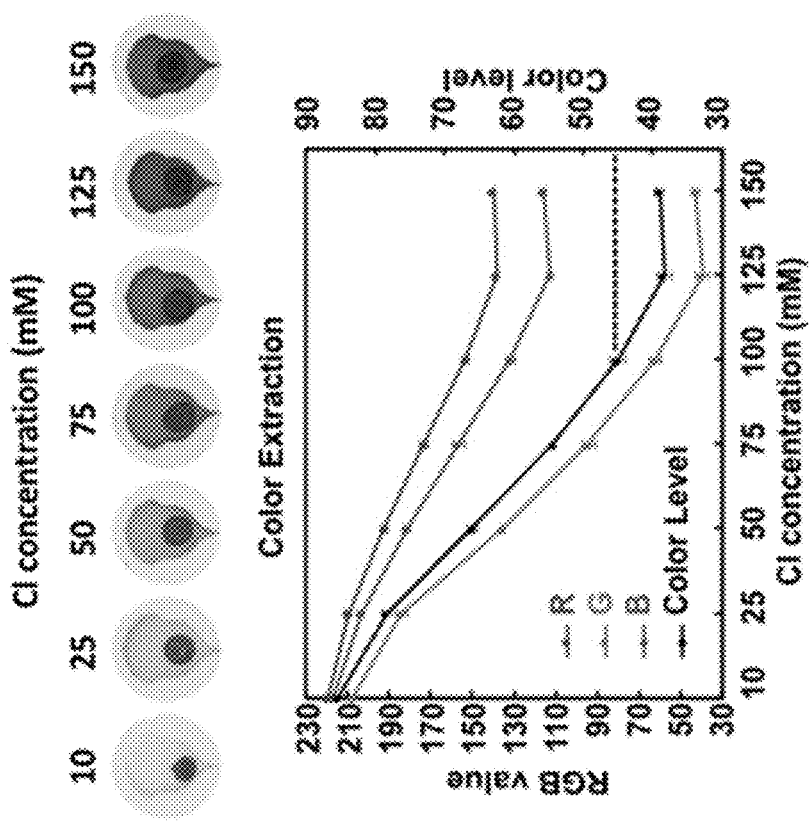
FIG. 11B The colorimetric assay increases in color intensity with increasing chloride concentration. When captured using a smartphone camera, the color provides a quantitative analysis of chloride levels.
Figure 11A:
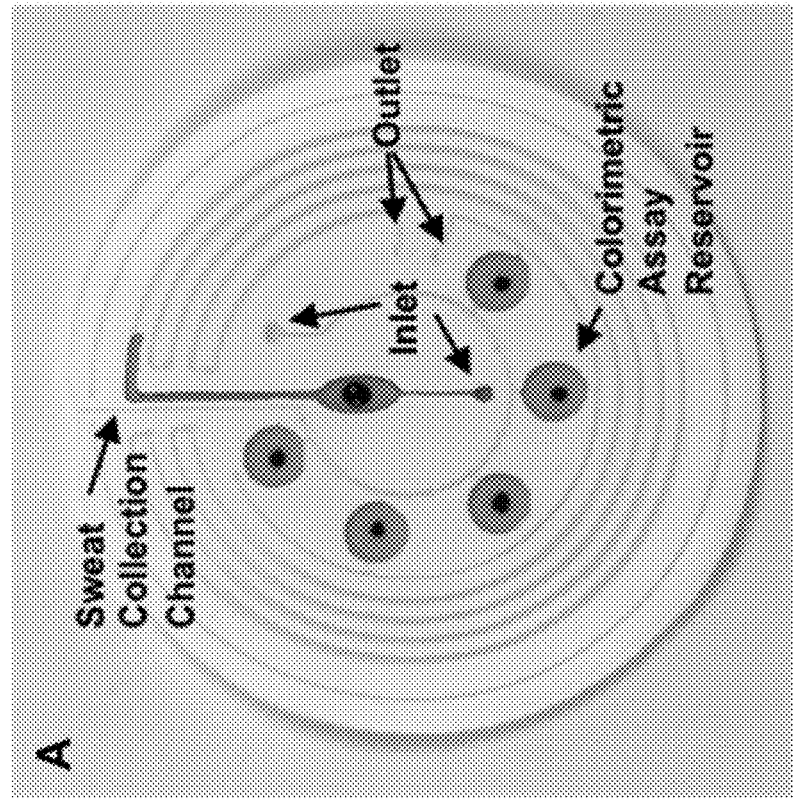
FIG. 11A provides an image of an epidermal collection device with integrated chloride colorimetric assay reservoirs.

The ability to integrate additional functionality beyond sweat collection offers a key advantage for epidermal microfluidic devices over the existing sweat collection methods. Reconfiguration of the epifluidic sweat collection device to include a colorimetric assay for the quantitative analysis of sweat chloride levels may significantly decrease the time-to-answer at the point-of-care for CF diagnostics or offering a facile method for an initial chloride level screen. FIG. 11A showcases this device variation which features an integrated colorimetric assay for chloride and an independent sweat collection chamber (70 µL volume). The colorimetric assay uses an excess of silver chloranilate for the quantitative analysis of chloride levels in sweat. The intensity of the violet color (FIG. 11B) increases with increasing sweat chloride levels. Imaging the assay reservoirs with a smartphone camera provides a simple method for rapidly quantifying the reservoir color by comparing the measured color with a calibrated color reference.

Figures 12A, 12B:
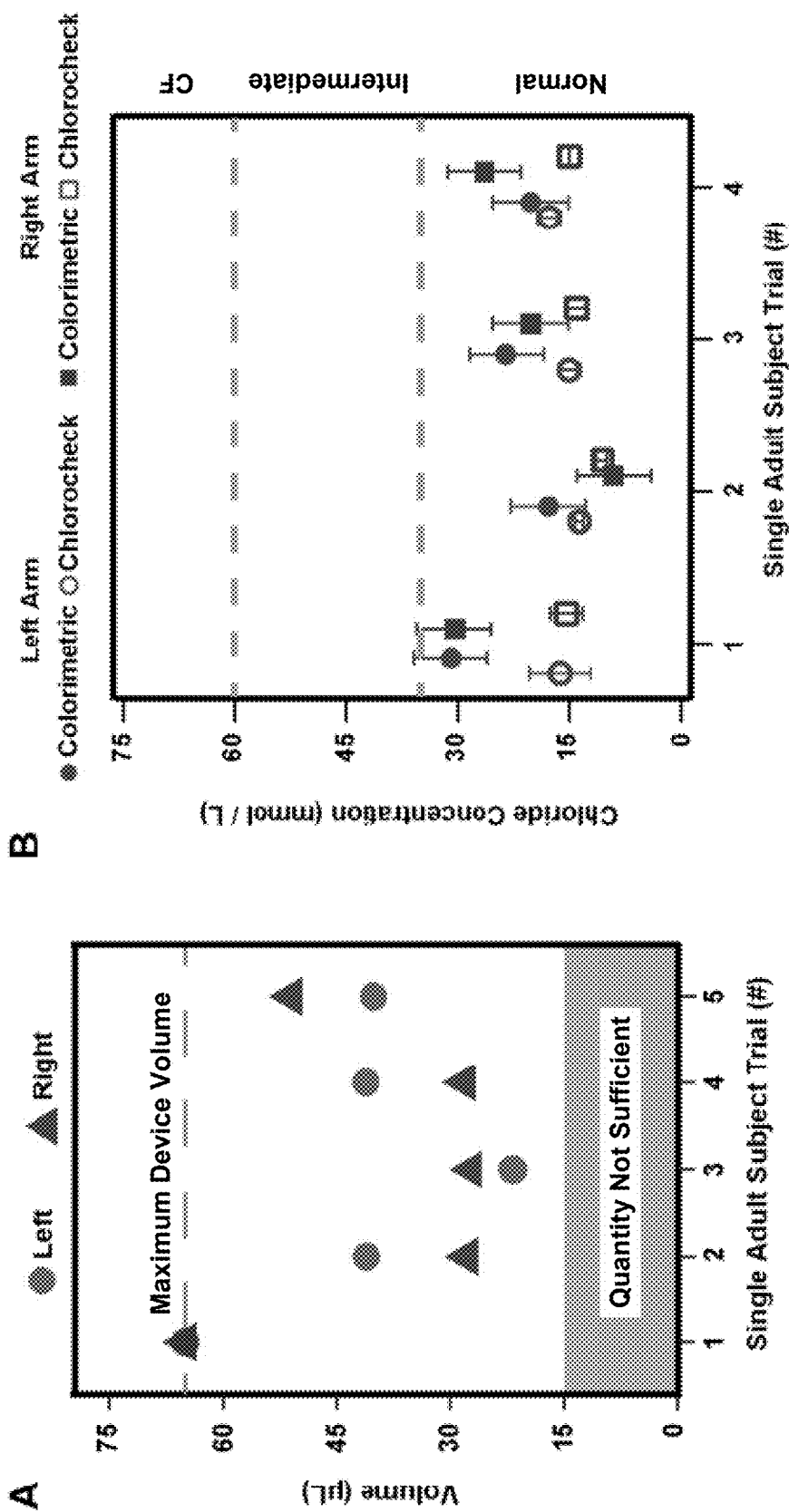
FIG. 12A Volume of collected sweat over a 5-day trial for a single adult volunteer using a collection device with integrated analysis.
FIG. 12B Comparison of colorimetric assay performance to ChloroChek® measurements over a 4-day trial for a single adult volunteer.

A small, one-person study of the sweat collection reproducibility of the device variation revealed lower volumes of collected sweat; however, no instants of QNS were recorded. This decrease in collection volume reflects the elimination of two additional collection points to provide independent colorimetric analysis of sweat chloride levels (FIG. 12A). FIG. 12B shows assay performance against the ChloroChek benchmark over a 4-day trial. Although the colorimetric assay results indicate an elevated level of chloride, as compared to the measurements from a chloridometer, the assay correctly indicates the absence of CF in the adult volunteer. As a screening method, this integration with an effective collection device offers a promising opportunity for on-board chloride screening.

STATEMENTS REGARDING INCORPORATION BY REFERENCE AND VARIATIONS

All references throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention. The specific embodiments provided herein are examples of useful embodiments of the present invention and it will be apparent to one skilled in the art that the present invention may be carried out using a large number of variations of the devices, device components, methods and steps set forth in the present description. As will be obvious to one of skill in the art, methods and devices useful for the present embodiments can include a large number of optional device components, compositions, materials, combinations and processing elements and steps.

Every device, system, combination of components or method described or exemplified herein can be used to practice the invention, unless otherwise stated.

Whenever a range is given in the specification, for example, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

When a group of substituents is disclosed herein, it is understood that all individual members of that group and all subgroups, including any device components, combinations, materials and/or compositions of the group members, are disclosed separately. When a Markush group or other grouping is used herein, all individual members of the group and all combinations and subcombinations possible of the group are intended to be individually included in the disclosure.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that compositions, materials, components, methods and/or processing steps other than those specifically exemplified can be employed in the practice of the invention without resort to undue experimentation. All art-known functional equivalents, of any such compositions, materials, components, methods and/or processing steps are intended to be included in this invention. The terms and expressions which have been employed are used as terms of description and not of limitation, and there is no intention in the use of such terms and expressions of excluding any equivalents of the features shown and described or portions thereof, but it is recognized that various modifications are within the scope of the invention claimed. Thus, it should be understood that although the present invention has been specifically disclosed by exemplary embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a layer" includes a plurality of layers and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

We claim:

1. A method for the detection of a biomarker in sweat comprising:
    providing an epidermal microfluidic device to a skin of a subject, wherein conformal contact is established thereby providing fluidic communication between said epidermal microfluidic device and said skin, said epidermal microfluidic device comprising:
        a flexible substrate comprising a first collection layer, a second collection layer and a capping layer disposed between the first collection layer and the second collection layer, wherein
            the first collection layer contains a first channel network forming at least one first collection chamber having a sweat inlet to being opened said skin and an outlet to the second collection layer, wherein said sweat inlet is operably in the fluidic communication with said skin;
            the second collection layer contains a second channel network forming a plurality of secondary collection chambers fluidically connected to the at least one first collection chamber, each of the secondary collection chambers having an inlet fluidically connected to said outlet of the at least one first collection chamber;
            the capping layer is formed to seal both the first channel network of the first collection layer and the second channel network of the second collection layer; and
            each of the first channel network and the second channel network is in a serpentine form; and
        an analyzer integrated with or fluidically connected to the at least one first collection chamber and/or the plurality of secondary collection chambers and configured to analyze said sweat for one or more biomarkers;
    collecting said sweat from said subject in said epidermal microfluidic device; and
    identifying or quantifying the amount of said one or more biomarkers in said sweat.

2. The method of claim 1, further comprising at least one of:
    measuring the volume of said sweat collected or the flow rate of said sweat from said subject; and
    monitoring a health condition of said subject based on said one or more biomarkers in said sweat.

3. The method of claim 2, wherein said one or more biomarkers are for i) monitoring or screening for cystic fibrosis, ii) monitoring drug or alcohol consumption, iii) monitoring dialysis efficacy, iv) monitoring glucose levels, v) monitoring creatinine levels, vi) monitoring urea levels, vii) monitoring pH or any combination thereof.

4. The method of claim 2, wherein the step of monitoring said health condition of said subject comprising monitoring a condition or disease, monitoring the efficacy of a treatment, monitoring the effect of a therapy or monitoring a physical condition.

5. The method of claim 1, wherein the step of identifying or quantifying the amount of said one or more biomarkers is performed in situ using said epidermal microfluidic device.

6. The method of claim 1, wherein the step of identifying or quantifying the amount of said one or more biomarkers is external laboratory based.

7. The method of claim 1, wherein said flexible substrate comprises a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, chitosan, and any combination thereof.

8. The method of claim 1, wherein said epidermal microfluidic device further comprises an adhesive layer, wherein the adhesive layer comprises an auxiliary hole that is through the adhesive layer that is in fluidic communication with the sweat inlet.

9. The method of claim 8, wherein the adhesive layer is capable of reversibly adhering to the skin surface.

10. The method of claim 8, wherein the adhesive layer comprises medical grade acrylic, silicone, hydrocolloid, or any combination thereof.

11. The method of claim 1, wherein said one or more biomarkers correspond to one or more of cystic fibrosis, presence or absence of alcohol, presence or absence of an illicit drug, and kidney or dialysis efficacy.

12. The method of claim 1, wherein said one or more biomarkers are one or more of a chloride, glucose, alcohol, an illicit drug, urea, creatine, or pH.

13. The method of claim 12, wherein the illicit drug is selected from the group consisting of marijuana, cocaine, heroin, lysergic acid diethylamide (LSD), psilocybin, methamphetamine, ketamine and a combination thereof.

14. The method of claim 1, wherein said epidermal microfluidic device further comprises a colorimetric sensor.

15. The method of claim 14, wherein the colorimetric sensor is a dye and said dye provides a visual representation of the amount of said sweat collected by said epidermal microfluidic device.

16. The method of claim 1, wherein said epidermal microfluidic device further comprises a plurality of colorimetric sensors.

17. The method of claim 16, wherein the colorimetric sensors comprise one or more color-responsive reagents for quantification of a sweat volume or amount, flow rate, composition or any combination of thereof, or for quantification of at least one of chloride, glucose, alcohol, an illicit drug, urea, creatinine or pH.

18. The method of claim 17, wherein the one or more color-responsive reagents are indicator reagents that react with said one or more biomarkers.

19. The method of claim 1, wherein each of the plurality of secondary chambers has one or more color-responsive reagents.

20. The method of claim 19, wherein the one or more color-responsive reagents are selected from the group consisting of dye, $CoCl_2$, glucose oxidase, peroxidase, potassium iodide, lactate dehydrogenase, diaphorase, formazan dyes, 2,4,6-tris(2-pyridiyl)-s-triazine (TPTZ) complexed with mercury ion or iron ion, a 2,2'-bicinchoninic acid, 1,10-phenanthroline, a universal pH indicator, silver chloranilate and any combination thereof.

21. The method of claim 1, wherein said epidermal microfluidic device further comprises one or more color calibration markers, ion-selective electrodes or electrochemical sensors, a temperature sensor, a wireless device, at least one light emitting diode (LED), or a combination thereof.

22. The method of claim 21, wherein said temperature sensor is embedded in or supported by said flexible substrate and provides a body temperature of said subject.

23. The method of claim 21, wherein said wireless device comprises a transmitter, a receiver, a transceiver, or a near-field communication (NFC) coil.

24. The method of claim 23, wherein said wireless device is wirelessly powered.

25. The method of claim 21, wherein said LED notifies said subject when collection of said sweat is complete or when said epidermal microfluidic device is full of said sweat, or when quantification or identification of said biomarker is complete.

26. The method of claim 1, wherein said subject is a human subject.

27. The method of claim 1, wherein said subject is a human subject undergoing a diagnostic procedure, a therapeutic procedure, a fitness activity, or monitoring the presence, onset or progression of a disease condition.

28. The method of claim 1, wherein said analyzer comprises one or more active components selected from the group consisting of a photodiode, a laser diode, a vertical cavity surface-emitting laser, a waveguide, and an optical resonance cavity.

29. The method of claim 1, wherein the plurality of secondary collection chambers is filled with said sweat flow in a sequential manner through a guide of series of capillary bursting valves.

* * * * *